United States Patent [19]
Lunsford et al.

[11] Patent Number: 5,827,314
[45] Date of Patent: *Oct. 27, 1998

[54] FLEXIBLE LIFTING APPARATUS

[75] Inventors: John P. Lunsford, San Carlos; Edwin J. Hlavka, Palo Alto; Edmund J. Roschak, Belmont; Daniel T. Wallace, San Francisco; Charles Gresl, Jr.; David B. McCallum, both of San Francisco; Dana G. Mead, Palo Alto, all of Calif.

[73] Assignee: Origin Medsystems, Inc., Menlo Park, Calif.

[ * ] Notice: The term of this patent shall not extend beyond the expiration date of Pat. No. 5,681,341.

[21] Appl. No.: 867,873

[22] Filed: Jun. 4, 1997

Related U.S. Application Data

[63] Continuation of Ser. No. 403,458, Mar. 14, 1995, Pat. No. 5,681,341.

[51] Int. Cl.$^6$ .................................................. A61M 29/00
[52] U.S. Cl. ........................... 606/192; 600/201; 604/103
[58] Field of Search .................................. 606/192, 196, 606/197; 600/201, 204, 207, 208; 609/103

[56] References Cited

U.S. PATENT DOCUMENTS

| | | | |
|---|---|---|---|
| 2,849,002 | 8/1958 | Oddo | 128/325 |
| 5,496,345 | 3/1996 | Kieturakis et al. | 606/192 |

Primary Examiner—Michael Buiz
Assistant Examiner—Daphna Shai
Attorney, Agent, or Firm—Limbach & Limbach LLP

[57] ABSTRACT

A lifting apparatus for deployment through a laparoscopic incision in a body wall to apply an external lifting force over a large area of the body wall. The apparatus provides a broad lifting surface that is capable of applying a lifting force of at least 40 pounds (180 Newtons) to an area of a body wall sufficiently extensive to reduce the lifting pressure exerted on the body wall to well below that which could cause pressure trauma to the body wall, yet delivers this broad lifting surface through the body wall via an incision about 14 mm long. The apparatus comprises a body wall engaging element capable of passing in a packaged state through the laparoscopic incision, and being inflatable to an inflated state. In the inflated state, the body wall engaging element is substantially toroidal, provides a broad lifting face, and bounds a central hole. The body wall engaging element includes an equatorial portion facing into the central hole. The apparatus also includes a flexible lifting element that has a flexible portion capable of passing through the laparoscopic incision. The flexible portion is attached to the equatorial portion of the body wall engaging element and extends from the equatorial portion towards the broad lifting face. The flexible lifting element also includes an adapter, connected to part of the flexible portion remote from the equatorial portion of the body wall engaging element, that receives the external lifting force and transfers the external lifting force to the flexible portion.

12 Claims, 17 Drawing Sheets

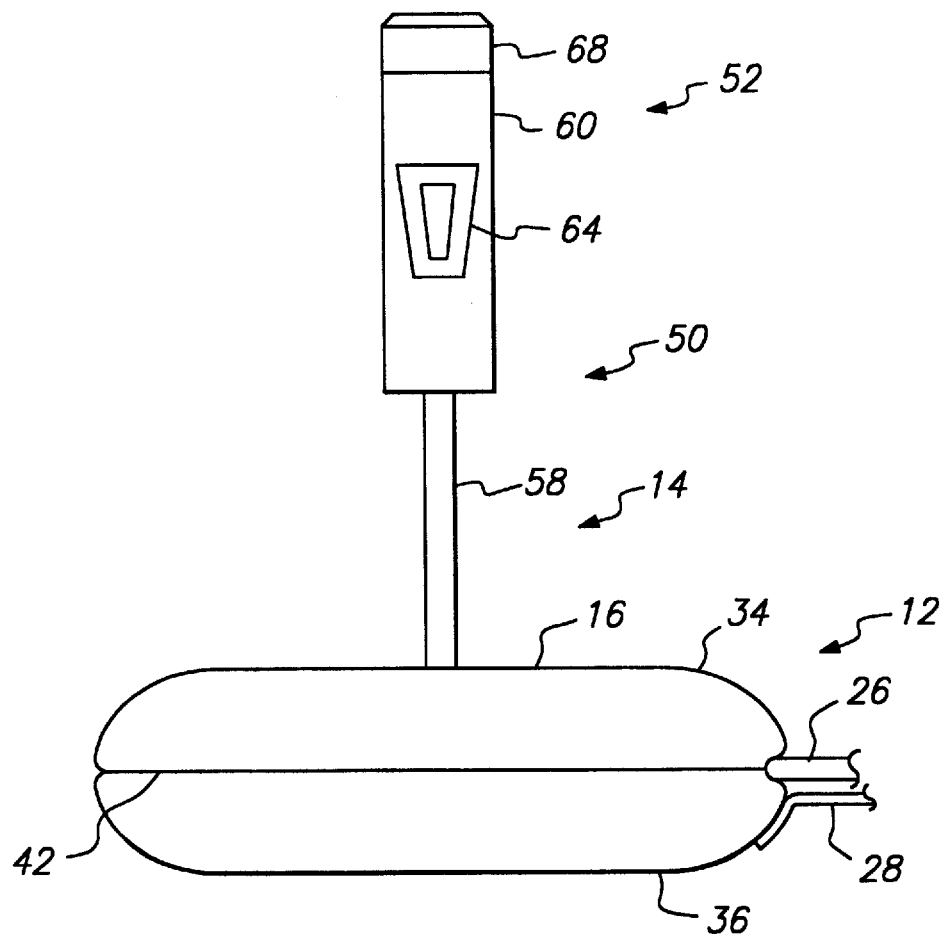
FIG. 1F
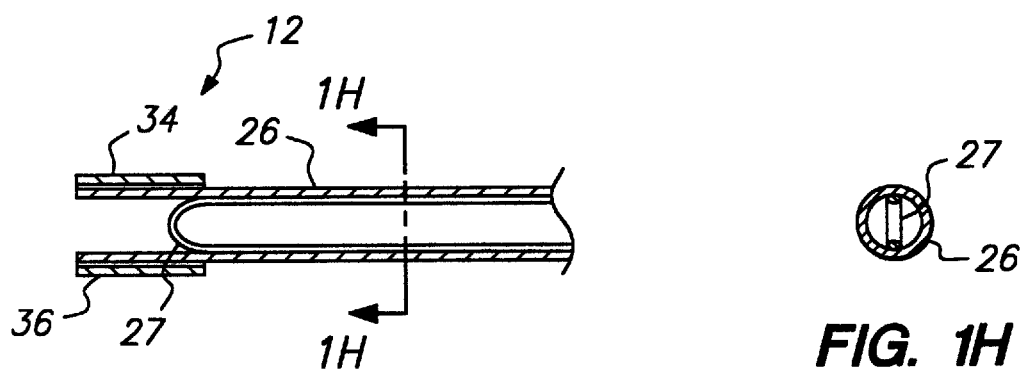
FIG. 1G
FIG. 1H

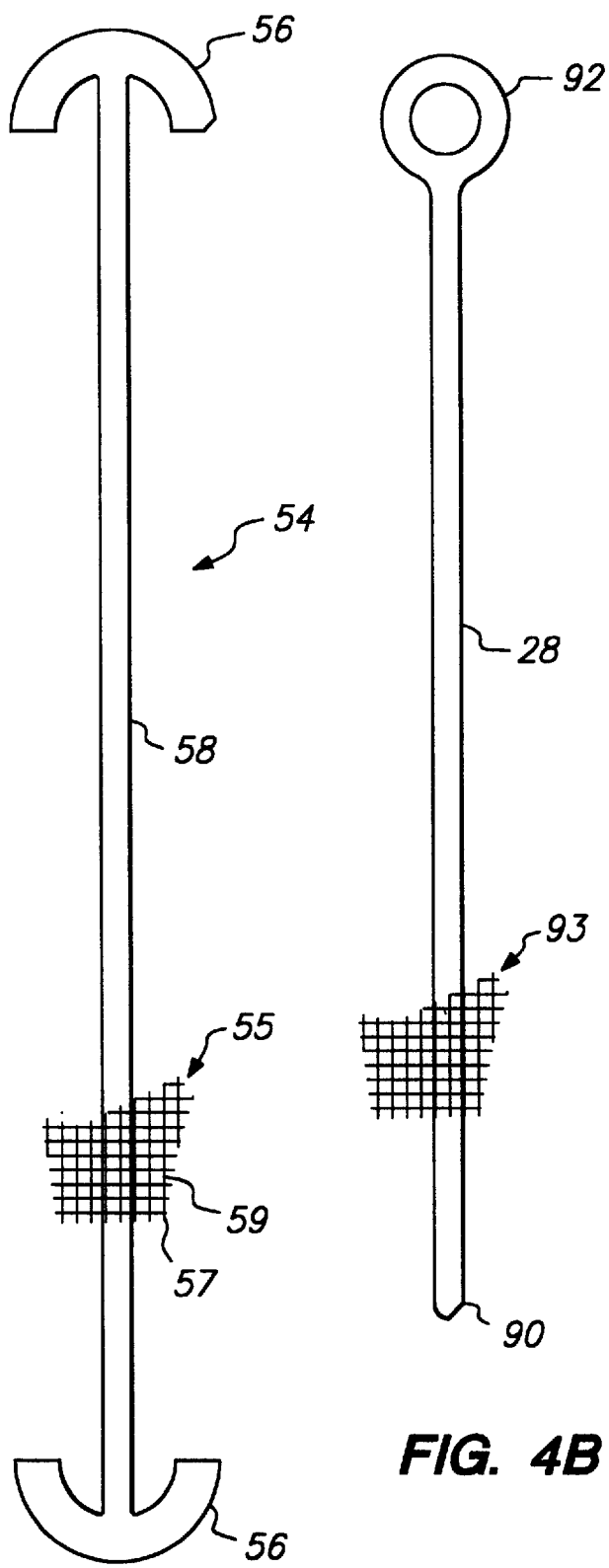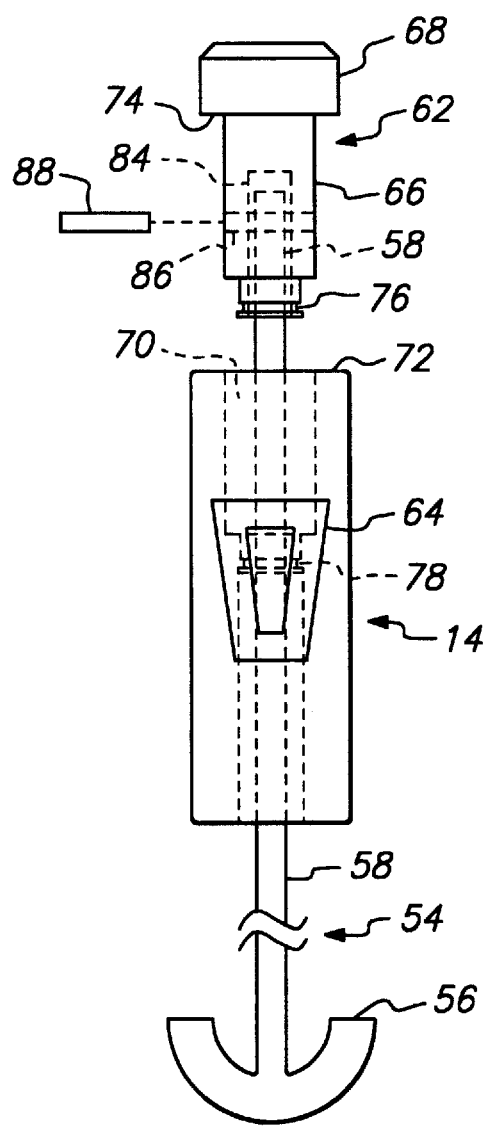
FIG. 4A
FIG. 4B
FIG. 5

FLEXIBLE LIFTING APPARATUS

This is a continuation of application Ser. No. 08/403,458, filed Mar. 14, 1995 U.S. Pat. No. 5,681,341.

FIELD OF THE INVENTION

The invention generally relates to an apparatus for lifting a body wall during surgery, especially during laparoscopic surgery.

BACKGROUND OF THE INVENTION

In the course of performing laparoscopic procedures in body cavities, such as the abdomen, it is necessary to raise the wall of the cavity to create space in which to work. A well-known method of raising the abdominal wall is to insufflate the abdominal cavity with a suitable insufflation gas, such as air, or carbon dioxide. A significant disadvantage of gas insufflation is that elongated instruments must be passed into the abdominal cavity through gas-tight seals, which significantly reduce the surgeon's feel of the instruments.

Several mechanical alternatives to gas insufflation have been proposed. The Gazayerli Endoscopic Retractor Model 1, described in SURGICAL LAPAROSCOPY AND ENDOSCOPY, Vol. 1, No. 2, 1991, pages 98–100, has a rigid rod with a hinged blade at the distal end. The blade can rotate through 360 degrees about an axis perpendicular to the long axis of the rod. The blade is aligned with the long axis of the rod for insertion into the abdomen through a small puncture. Once inside the abdomen, the blade is swivelled through about 90 degrees to form a T-shaped structure. The proximal end of the rod can be raised by hand or by a rope, pulley and weight arrangement. Raising the rod causes the blade to engage the abdominal wall and to lift it.

French patent application no. 90-03980 shows a wire structure that is threaded into the abdomen through a small puncture to engage and to lift the abdominal wall. The application also shows a fan retractor that has a first angle-shaped member having a first leg that engages with the abdominal wall, a tubular second leg having a bore, and a third leg, remote from the first leg, that has a hook-shaped member on its end distal from the second leg. A second angle-shaped member has a first leg that engages with the abdominal wall, a second leg that pivots within the bore of the second leg of the first angle-shaped member, and a third leg, remote from the first leg, that serves as an operating lever for the second angle-shaped member. The first legs of the angle-shaped members are closed together to insert them into the abdominal cavity through an incision. The third leg of the second angle-shaped member is then operated to spread the first leg of the second angle-shaped member apart from the first leg of the first angle-shaped member. The first legs are engaged with the peritoneum inside the abdominal cavity. A lifting force is then applied to the hook-shaped member to lift the retractor and hence to lift the abdominal wall.

U.S. patent application Ser. No. 08/062,707, assigned to the assignee of this application, describes a number of different mechanical devices that are inserted through one or more punctures into the abdomen. All or part of the device is then lifted to lift the abdominal wall away from the underlying abdominal organs. One of the devices described in this application is a fan retractor that is inserted in a closed condition into the abdominal cavity, spread apart once inside the abdominal cavity, and brought into contact with the peritoneum inside the abdominal cavity. The apparatus is then lifted to lift the abdominal wall.

The above-mentioned fan retractors can be used with intra-abdominal placement. Because the peritoneum-engaging elements of such devices are relatively elongated, it is possible to snag the bowel or omentum during deployment. Under some circumstances, it may be necessary to make multiple attempts at inserting the retractor before the fan retractor can be correctly positioned with its peritoneum-engaging elements adjacent to the peritoneum with no bowel or omentum caught between the peritoneum-engaging elements and the peritoneum. Insufflating the abdomen before inserting the fan retractor does not necessarily eliminate the risk of snagging.

U.S. patent application Ser. No. 07/890,033, assigned to the assignee of this application, describes a fan retractor that can be inserted into the abdomen properitoneally to prevent snagging. The abdominal wall contacting legs of the fan retractor are shaped to enable them to dissect the peritoneum away from the abdominal wall so that the peritoneum can act as a drape over the underlying organs. In addition, the legs are shaped to provide a stiffness that decreases away from the pivot to enable the legs to conform to the internal shape of the abdominal wall.

The known mechanical lifting devices described above generally expose a smaller area of the underlying organs than conventional gas insufflation. Moreover, the known mechanical lifting devices are inserted into the abdomen through a laparoscopic incision. Consequently, due to the dimensional constraints imposed by the need to pass though such a small incision, these devices apply the lifting force to a relatively small area of the abdominal wall, and, consequently, expose the small area of the abdominal wall to a relatively high lifting pressure.

U.S. patent application Ser. No. 08/238,348, assigned to the assignee of this application, hereinafter the "prior application," the disclosure of which is incorporated herein by reference, describes an inflatable lifting apparatus that has a flat lifting surface. The inflatable lifting apparatus is intended for deployment through a laparoscopic incision in a body wall to apply an external lifting force over a large area of the body wall. The apparatus has a body wall engaging element and an elongate lifting tube. The body wall engaging element is shaped to pass in a packaged state through the laparoscopic incision in the body wall. The body wall engaging element is inflatable to an inflated state, and includes, in the inflated state, a plane lifting surface. The lifting tube includes a distal portion that is connected to the lifting surface of the body wall engaging element, and is also shaped to pass through the laparoscopic incision. The lifting tube also includes a proximal portion that receives the external lifting force in a direction that moves the body wall engaging element into contact with the body wall.

The inflatable lifting apparatus described in the prior application overcomes many of the disadvantages of the purely mechanical lifting devices. The elongate lifting tube is hollow, and provides access to the body cavity for a surgical instrument. However, a rigid lifting tube limits lateral and angular movement of an instrument inserted therein. To overcome this difficulty, instrument ports are provided in the body wall engaging element. However, using these instrument ports requires that additional laparoscopic incisions be made in the body wall. Moreover, movement of a instrument inserted through an instrument port is still partially constrained, because the lifting tube can obstruct movement of the instrument.

The body wall engaging element of the inflatable apparatus described in the prior application is preferably constructed from a relatively thin material to make the body wall engaging extremely compact in its collapsed state. The thin material, however, may limit the maximum inflation pressure that can be reliably used. The body wall engaging element has a complex internal structure of baffles to enable it to assert the required lifting force against the body wall when inflated to a relatively low inflation pressure. The baffles increase the bulk of the body wall engaging element in its collapsed state, and make the body wall engaging element complex to manufacture.

Finally, at the end of the procedure, the collapsed body wall engaging element of the inflatable lifting apparatus described in the prior application may require a considerable tractive force applied to the lifting tube to remove it from the body cavity through the laparoscopic incision.

SUMMARY OF THE INVENTION

The present invention provides a lifting apparatus that fulfills two main performance requirements that conflict with one another. The lifting apparatus includes a broad lifting surface that is capable of applying a lifting force of at least 40 pounds (180 Newtons) to an area of a body wall that is sufficiently extensive that the lifting pressure exerted on the body wall is well below that which could cause pressure trauma to the body wall. The lifting apparatus delivers this broad lifting surface into the body cavity underlying the body wall through an incision in the body wall about 14 mm long.

The present invention additionally provides a lifting apparatus that retains the advantages of the inflating lifting apparatus described in the prior application, and which has additional operational advantages. These advantages include an improved access for surgical instruments without the need for additional incisions, and a greater freedom of movement for surgical instruments, including allowing surgical instruments to be inserted at an oblique angle. The lifting apparatus according to the present invention additionally allows the patient to move or be moved relative to the lifting arm, and enables the body wall to be disposed at different angles relative to the direction of lift. Finally, the lifting apparatus according to the present invention provides an improved ease of manufacture.

Accordingly, the invention provides an apparatus for deployment through a laparoscopic incision in a body wall to apply an external lifting force over a large area of the body wall. The apparatus comprises a body wall engaging element capable of passing in a packaged state through the laparoscopic incision, and being inflatable to an inflated state. In the inflated state, the body wall engaging element is substantially toroidal, provides a broad lifting face, and bounds a central hole. The body wall engaging element includes an equatorial portion facing into the central hole. The apparatus also includes a flexible lifting element that has a flexible portion capable of passing through the laparoscopic incision. The flexible portion is attached to the equatorial portion of the body wall engaging element and extends from the equatorial portion towards the broad lifting face. The flexible lifting element also includes an adapter, connected to part of the flexible portion remote from the equatorial portion of the body wall engaging element, that receives the external lifting force and transfers the external lifting force to the flexible portion.

The invention also provides a method of packaging a lifting apparatus for deployment through a laparoscopic incision. In the method, a lifting apparatus is provided comprising a flat, substantially circular or elliptical body wall engaging element having a center, an outer periphery, and opposed faces, and having a flexible lifting element attached to approximately the center and extending from one of the faces. An elongate pouch is also provided having an open end and having on one side a central aperture and on the other side a longitudinal line of perforations. The body wall engaging element is rolled from diametrically opposed points on the outer periphery towards the center. After rolling, the body wall engaging element is substantially cylindrical. The flexible lifting element is threaded into the open end of the pouch and out of the central aperture of the pouch. Finally, the rolled body wall engaging element is inserted into the pouch, which retains it in its rolled state.

Finally, the invention provides a method of applying an external lifting force of greater than ten pounds to a large area of a body wall to lift the body wall. The external lifting force being applied to the body wall through a laparoscopic incision in the body wall. In the method, a lifting apparatus is provided. The lifting apparatus includes a body wall engaging element in a packaged state, capable of passing through the laparoscopic incision. The body wall engaging element is inflatable from the packaged state to an inflated state in which the body wall engaging element is substantially toroidal, provides a broad lifting face, and bounds a central hole. The lifting apparatus also includes a flexible lifting element that has a flexible portion capable of passing through the laparoscopic incision and an adapter. The flexible portion is attached to the equatorial portion of the body wall engaging element and extends from the equatorial portion towards the broad lifting face. The adapter is connected to part of the flexible portion remote from the equatorial portion of the body wall engaging element, receives the external lifting force, and transfers the external lifting force to the flexible portion. The packaged body wall engaging element and part of the flexible lifting element are advanced through the laparoscopic incision. The body wall engaging element is inflated to an inflated state to provide a broad lifting surface. Finally, the external lifting force is applied to the adapter of the flexible lifting element to move the broad lifting surface into contact with the body wall and to lift the body wall from a normal state to a lifted state.

BRIEF DESCRIPTION OF THE DRAWINGS

FIG. 1F is a side view of the preferred embodiment of the lifting apparatus according to the invention in its inflated state.

FIG. 1G is a longitudinal cross-sectional view of part of the inflation tube of the preferred embodiment of the lifting apparatus according to the invention showing an anti-kinking device.

FIG. 1H is a transverse cross-sectional view of part of the inflation tube of the preferred embodiment of the lifting apparatus according to the invention showing the anti-kinking device.

FIG. 4A is a plan view of the epsilon of the preferred embodiment of the lifting apparatus according to the invention, prior to attachment to the body wall engaging element and the arm attachment element.

FIG. 4B is a plan view of the tether of the preferred embodiment of the lifting apparatus according to the invention, prior to attachment to the body wall engaging element.

FIG. 5 is an exploded side view of the flexible lifting element of the preferred embodiment of the lifting apparatus according to the invention, prior to attachment of the semi-annular portions of the epsilon to the body wall engaging element.

FIG. 11A shows the location of the incision in the abdominal wall.

FIG. 11B shows the distal end of the packaged body wall engaging element entering the incision.

FIG. 11C shows the orientation of the packaged body wall engaging element changing as the insertion progresses.

FIG. 11D shows the location of the packaged body wall engaging element relative to the abdominal wall following insertion.

FIG. 11E shows the flexible lifting element being pulled to relocate the packaged body wall engaging element relative to the incision.

FIG. 11F shows inflation of the body wall engaging element.

FIG. 11G shows attachment of the lifting apparatus to the lifting arm.

FIG. 11H shows the lifting apparatus used to lift the abdominal wall.

FIG. 11I shows how the lifting apparatus provides access for an instrument to the working space created by lifting the abdominal wall. FIG. 11I also illustrates how part of the flexible portion of the flexible lifting element can be moved to prevent it from obstructing movement of the instrument.

FIG. 11J shows the abdominal wall returned to the normal (non-lifted) state and the body wall engaging element partially deflated.

FIG. 11K shows the tether pulled proximally to relocate the collapsed body wall engaging element relative to the incision.

FIG. 11L shows the tether pulled further proximally to remove the collapsed body wall engaging element edge-first from the incision.

DETAILED DESCRIPTION OF THE INVENTION

The preferred embodiment of the lifting apparatus 10 according to the invention is shown in its operational state in FIGS. 1A–1F, in which perspective, top, bottom, cross sectional, and elevational views are respectively shown. The lifting apparatus 10 has two main components, the body wall engaging element 12 and the flexible lifting element 14, as shown in the perspective view of FIG. 1A. Additional details of the components of the lifting apparatus 10 are shown in FIGS. 3, 4A, 4B, and 5.

Figures 2A, 2B, 2C:
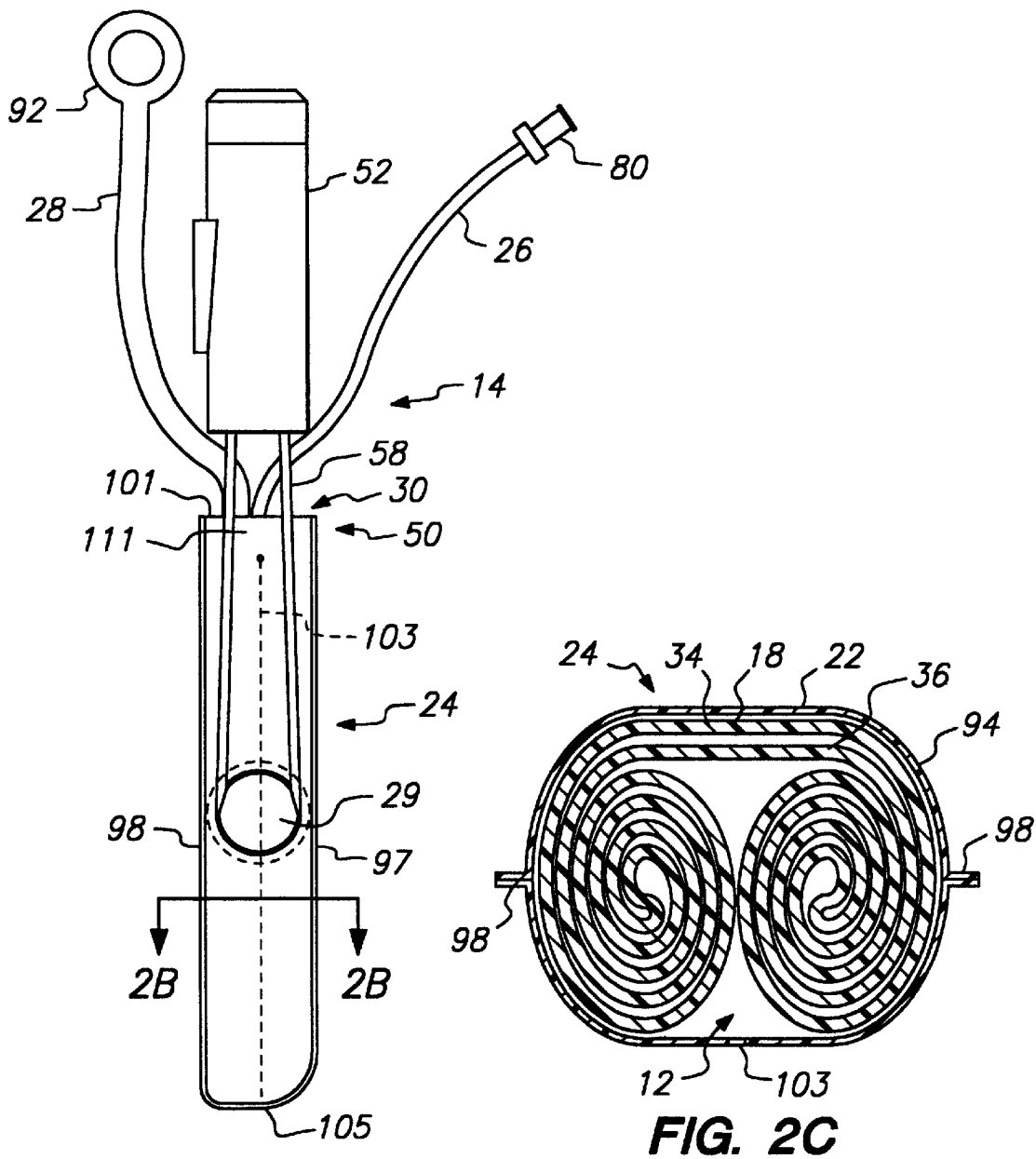
FIGS. 2A–2C are respectively a side view, a cross-sectional view and an enlarged cross-sectional view of the preferred embodiment of the lifting apparatus according to the invention with the body wall engaging element in its packaged state.

The lifting apparatus 10 is also shown in its packaged state, prior to insertion into the body cavity in FIGS. 2A–2C. In the packaged state shown in FIG. 2A–2C, the envelope 18 of the body wall engaging element 12 is tightly rolled, as shown in the cross-sectional view of FIG. 2B and in the enlarged cross-sectional view of FIG. 2C, and is retained in this state by the pouch 22 to form the package 24. The flexible lifting element 14 extends from the aperture 29 mid-way along the side of the package 24, and the inflation tube 26 and the tether 28 extend from the proximal end 30 of the package, as will be described in more detail below. In the package 24, the body wall engaging element 12 will pass easily through a laparoscopic incision in the body wall into the underlying body cavity, for example, into the abdominal cavity.

To minimize trauma to the patient, the laparoscopic incision should be as small as possible. Consequently, it is desirable that the cross-sectional area of the package 24 be minimized because the cross-sectional area of the package determines the size of the incision. In the lifting apparatus according to the invention, the package 24 containing a body wall engaging element 12 capable of exerting a lifting force of at least 40 pounds (180 N) can be inserted through a laparoscopic incision about 14 mm long.

After the package 24 has been inserted though the incision, and all the package lies inside the body cavity, gentle force is applied to the flexible lifting element 14 to align the center of the aperture 29, and, hence the center of the body wall engaging element 12, with the incision. Then, an inflation fluid is passed through the inflation tube 26 into the body wall engaging element 12. This releases the body wall engaging element from the pouch 22, and inflates the body wall engaging element to the inflated state shown in FIGS. 1A–1F. In the inflation process, the body wall engaging element 14 expands to juxtapose the lifting surface 16 with the body wall. The lifting surface has an area about 60 times that of the transverse cross-sectional area of the package 24.

Once the body wall engaging element 12 is fully inflated, the flexible Lifting element 14 is attached to a suitable lifting arm (not shown). The lifting arm applies the lifting force to the flexible lifting element 14. The flexible lifting element 14 transmits the lifting force to the body wall engaging element 12. The body wall engaging element transfers the lifting force to the body wall (not shown) via the broad, flat lifting surface 16 and lifts the body wall. The large area of the lifting surface 16 of the body wall engaging element 12 distributes the lifting force substantially uniformly over a large area of the body wall. As a result, the lifting apparatus according to the invention applies a considerably lower lifting pressure to the body wall than is applied by the mechanical lifting devices described above.

In its inflated state, the body wall engaging element 12 is toroidal and has a substantially elliptical cross section. The toroidal body wall engaging element bounds the central hole 32. Instruments and endoscopes can be passed though the incision and the central hole 32 to perform surgical procedures in the working space created by the lifting apparatus 10 lifting the body wall. If the flexible lifting element 14 obstructs movement of an instrument, the flexible lifting element is flexible, so can easily be moved out of the way.

Following the end of the procedure, the lifting force is removed, which returns the body wall to its normal (non-lifted) state. The flexible lifting element 14 is released from the lifting arm, the inflation fluid is released from the body wall engaging element 12, and the body wall engaging element is evacuated to minimize its volume. The proximal end of the tether 28, which remains outside the body cavity during the treatment procedure, is gently pulled axially to align part of the perimeter of the envelope 18 with the laparoscopic incision. Further gentle tension on the tether 28 withdraws the envelope from the body cavity through the incision. In the course of withdrawing the envelope through the incision, the part of the flexible lifting element 14 that was inside the body cavity is also withdrawn. Once the lifting apparatus has been withdrawn from the incision, the incision is closed in the normal way.

Details of the construction of the lifting apparatus 10 according to the invention will now be described with reference to FIGS. 1A–1F. The body wall engaging element 12 will be described first.

The body wall engaging element 12 is substantially toroidal. The toroid has a substantially elliptical cross section. The minor axis of the ellipse is aligned with the lifting direction and is preferably about one half of the length of the major axis. This shape provides the body wall engaging element with the broad lifting surface 16 while affording access through the central hole 32 to the working space created by lifting the body wall. The central hole is located relative to the flexible lifting element 14 such that, when the body wall is lifted, the central hole is aligned with the incision through which the flexible lifting element 14 passes through the body wall (and through which the body wall engaging element 12 was inserted into the body cavity underlying the body wall). This alignment enables instruments inserted into the incision to reach the working space underlying the body wall engaging element via the central hole 32.

The lifting surface 16 is more curved than that of the body wall engaging element of the inflating lifting apparatus described in the prior application. However, this curvature does not significantly increase the lifting pressure applied to the body wall by the lifting surface 16 relative to that applied by a flat lifting surface. This is because inflatable body wall engaging elements have an intrinsic limitation on the lifting pressure applied to the body wall, namely, the inflation pressure. The body wall engaging element 12 deforms in response to the lifting force until the area of the lifting surface 16 in contact with the body wall increases to that required to transfer all the lifting force to the body wall. The inflation pressure used in the lifting apparatus according to the invention, although larger than that used in the apparatus with the flat lifting surface described above, is well below that at which the lifting pressure applied to the body wall could cause pressure trauma to the body wall.

The body wall engaging element 12 lacks the internal baffles of the body wall engaging element of the inflating lifting apparatus described in the prior application, and is therefore considerably simpler, consisting of the upper envelope half 34 and the lower envelope half 36 forming the envelope 18. The stiffness required for the body wall engaging element 12 to transfer the lifting force to the body wall is provided by using a considerably increased inflation pressure. The envelope halves 34 and 36 use a new composite material that has the strength and resistance to leakage required to provide reliability in spite of the increase in inflation pressure. The new envelope material is thicker than the envelope material used in the flat-surface lifting apparatus, but since the body wall engaging element 12 lacks internal baffles, it uses fewer square inches of envelope material, and the bulk of the package 24 is little different from that of the package of the flat-surface lifting apparatus. Eliminating the internal baffles not only makes the lifting apparatus according to the invention easier to manufacture, it also increases potential reliability, because the number of welded joints, each of which may fail, is substantially reduced.

The composite material of the envelope halves 34 and 36 is required to have a combination of strength, flexibility, suppleness, low bulk, weldability, and resistance to leakage. Polyamide, such as nylon, has the necessary strength requirements but is almost impossible to weld. Polyamide fiber has tensile strength advantages over polyamide film at the expense of greater thickness. Polyurethane has the required flexibility and weldability requirements, but has poor strength characteristics. A composite of these materials provides the advantages of both materials.

Initial embodiments were made from a composite material formed by laminating an open-weave fabric made of 200 denier monofilament nylon with about 20–30 threads/inch (8–12 threads/cm) between two layers of polyurethane film about 4 mil. (100 $\mu$m) thick using heat and pressure. This composite material had excellent strength characteristics and the bulk material had very low leakage. However, the relative stiffness of the nylon monofilaments led to leakage problems when the material was welded. Welding released the monofilaments from the polyurethane matrix, and the voids left in the polyurethane matrix provided a leakage path for the inflation fluid. Leakage was reduced by substituting 200 denier spun nylon thread for the nylon monofilaments in the fabric. A further improvement in strength characteristics was obtained by using a more closely woven fabric of 200 denier spun nylon thread with 60×45 threads per inch (24×18 threads/cm). The fabric was heat and pressure laminated between two 4 mil. (100 $\mu$m) layers of polyurethane to form an envelope material that was nominally 14 mil. (300 $\mu$m) thick.

The upper envelope half 34 and the lower envelope half 36 are annular and are welded together at their inner peripheries 44 and at their outer peripheries 45 to form a toroidal chamber. Because of the threads in the composite envelope material form a square matrix, the body wall engaging element 12 tends to assume a square shape when inflated. This shape may be optimum in some applications. The body wall engaging element 12 can be made round for applications that require this shape by orienting the threads of the upper envelope half 34 at about 45 degrees to the threads of the lower envelope half 36 prior to welding the envelope halves together. The directions in which the threads run in the upper envelope half 34 and in the lower envelope half 36 are respectively shown by the area 20 in the top view of FIG. 1B and the area 21 in the bottom view of FIG. 1C.

Figure 3A:
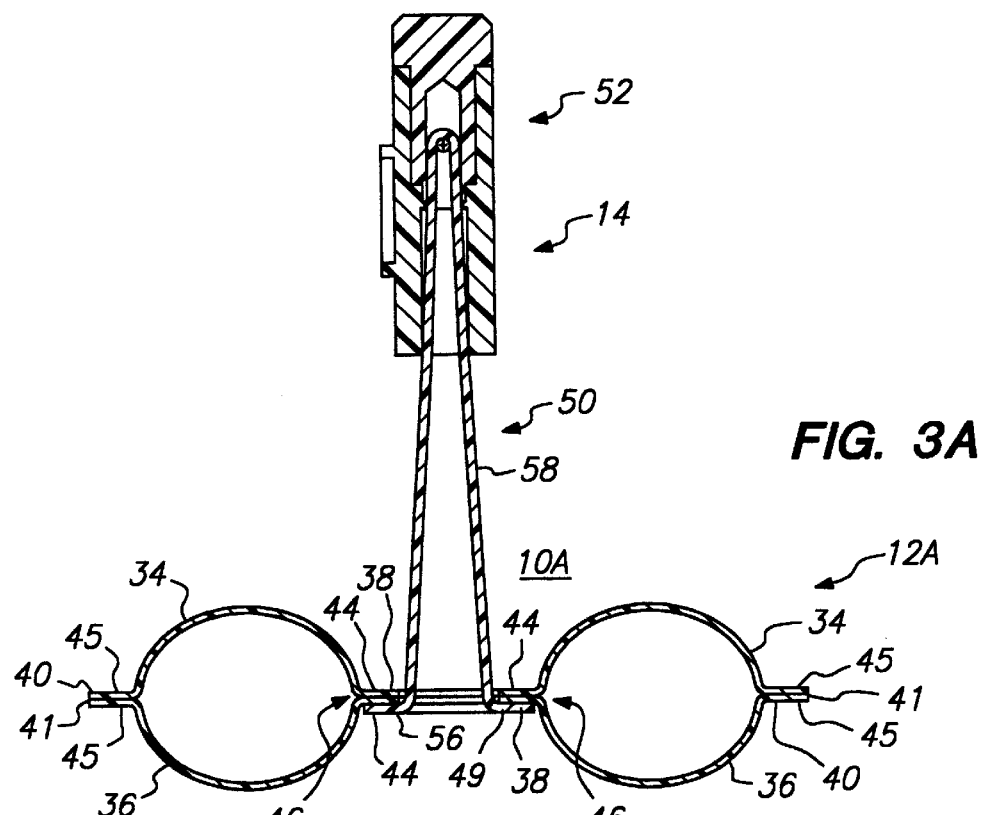
FIGS. 3A and 3B are respectively a vertical cross section and a side view of an embodiment of the lifting apparatus according to the invention with a first alternative embodiment of the body wall engaging element shown in its inflated state. In this embodiment, the outer seam of the body wall engaging element is not housed inside the body wall engaging element.
Figure 3B:
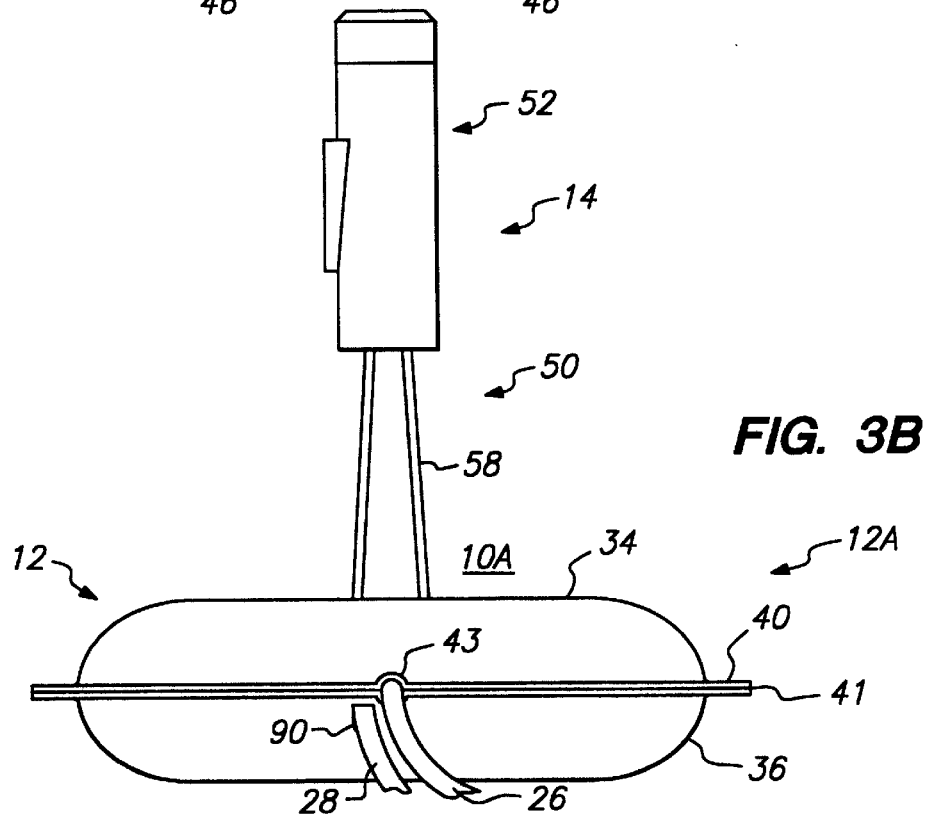

The upper envelope half 34 may be welded to the lower envelope half 36 as shown in FIGS. 3A and 3B. In FIGS. 3A and 3B, parts that are identical to those shown in FIGS. 1A–1F are indicated by the same reference numeral, and parts that are similar are indicated by the same reference numeral with the letter "A" added. The way of welding the envelope halves together shown in FIGS. 3A and 3B is simplest because both the inner seam 38 and the outer seam 40 can be welded in one operation. When the envelope halves are welded this way, the outer seam 40 projects outwards from the body wall engaging element 12A and, when the body wall engaging element is inflated, is relatively rigid. Moreover, the nylon fibres in the envelope material give the outer seam a rough outer edge 41. Additional processing, such as flame treatment, or welding a thin cover over the outer edge, must therefore be performed to provide the outer seam with a smooth outer edge.

Figure 1A:
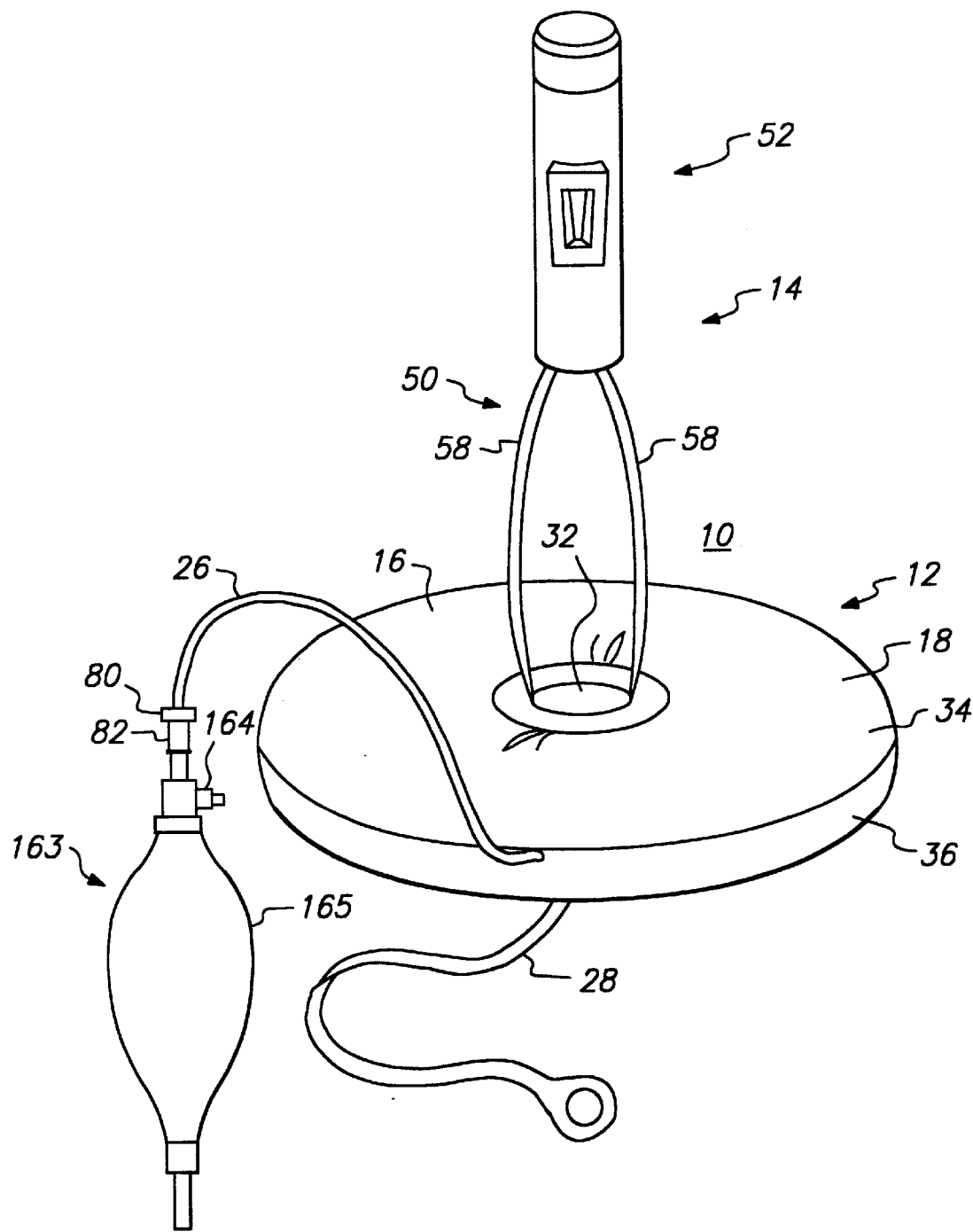
FIG. 1A is a perspective view of the preferred embodiment of the lifting apparatus according to the invention in its inflated state.
Figure 1B:
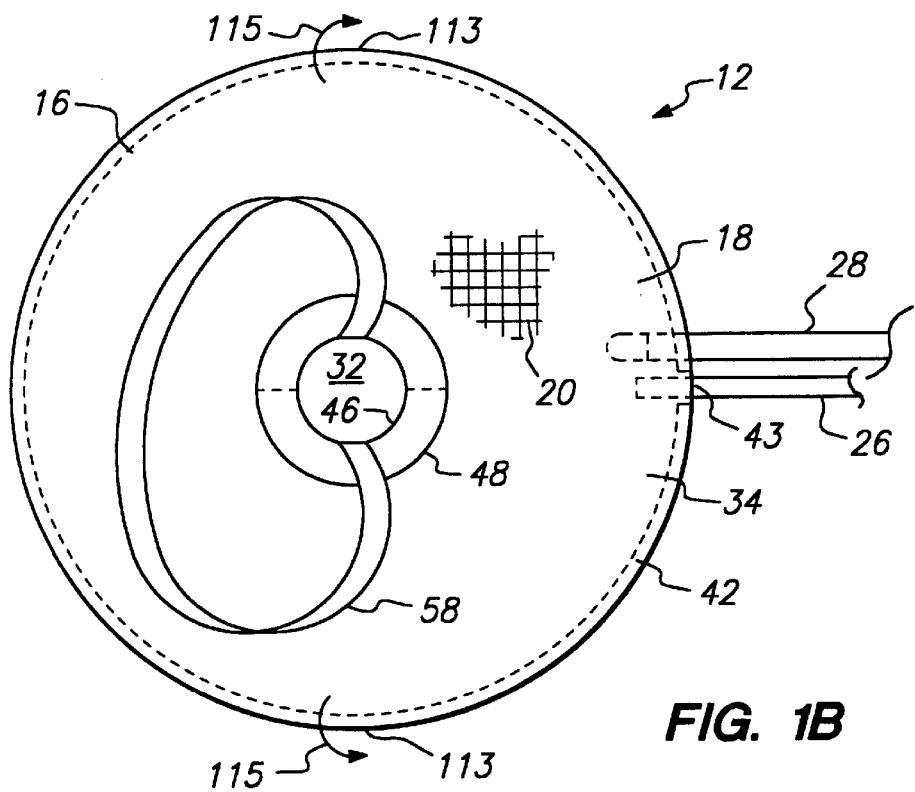
FIG. 1B is a top view of the preferred embodiment of the lifting apparatus according to the invention in its inflated state. The arm attachment element is omitted for clarity.
Figure 1C:
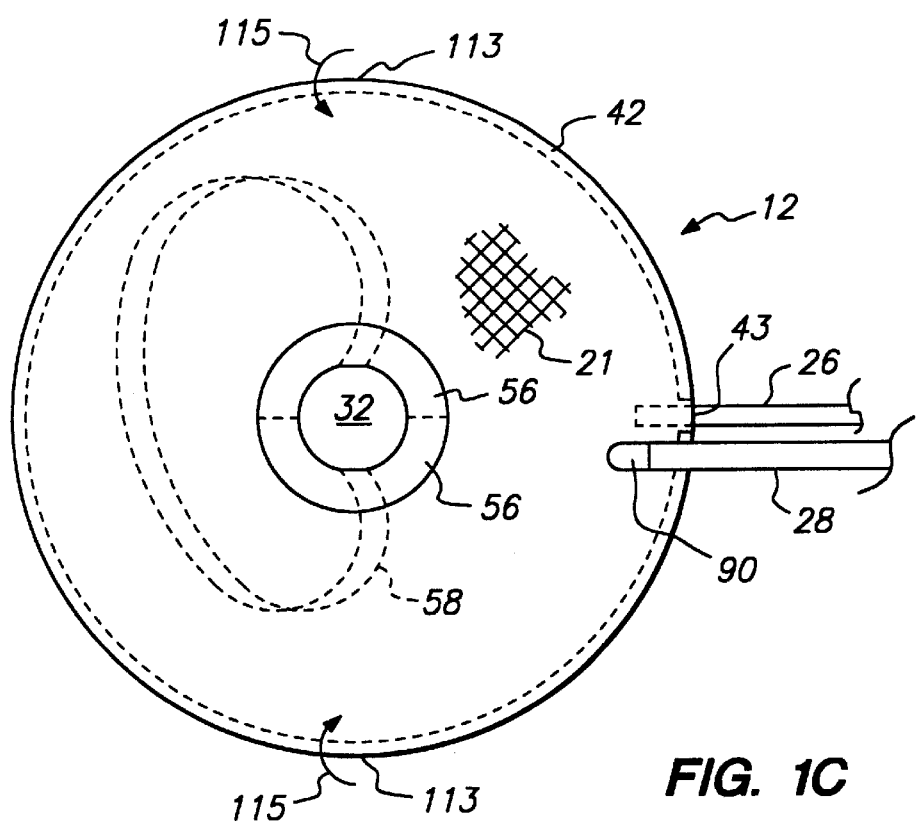
FIG. 1C is a bottom view of the preferred embodiment of the lifting apparatus according to the invention in its inflated state. The arm attachment element is omitted for clarity.
Figure 1D:
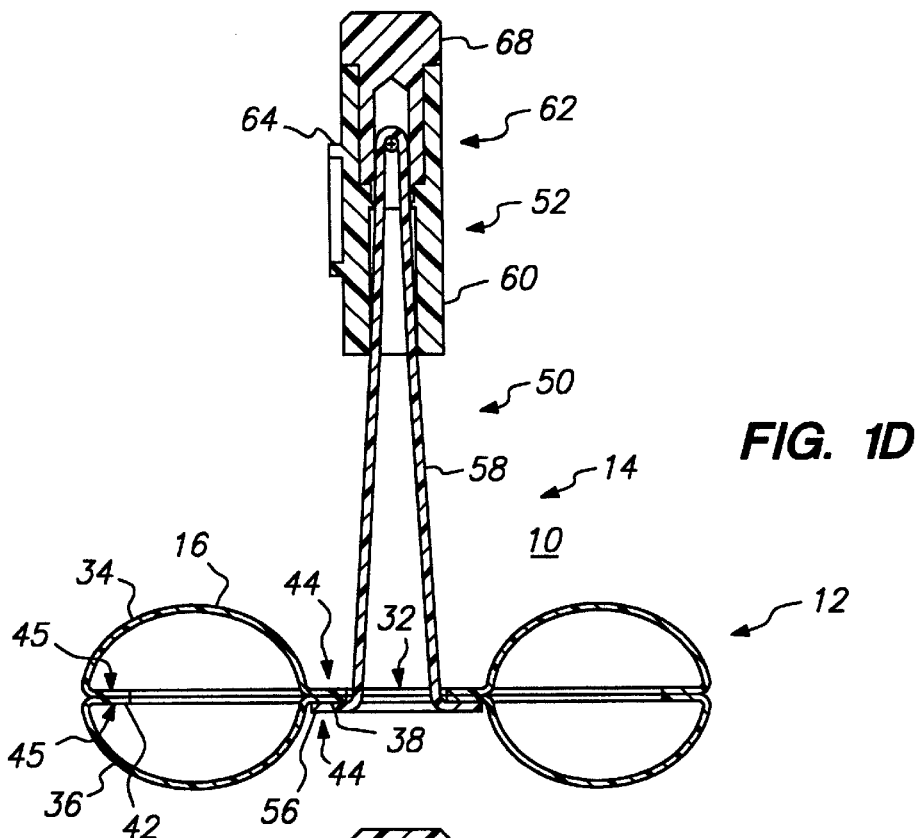
FIG. 1D is a first cross-sectional view of the preferred embodiment of the lifting apparatus according to the invention in its inflated state.
Figure 1E:
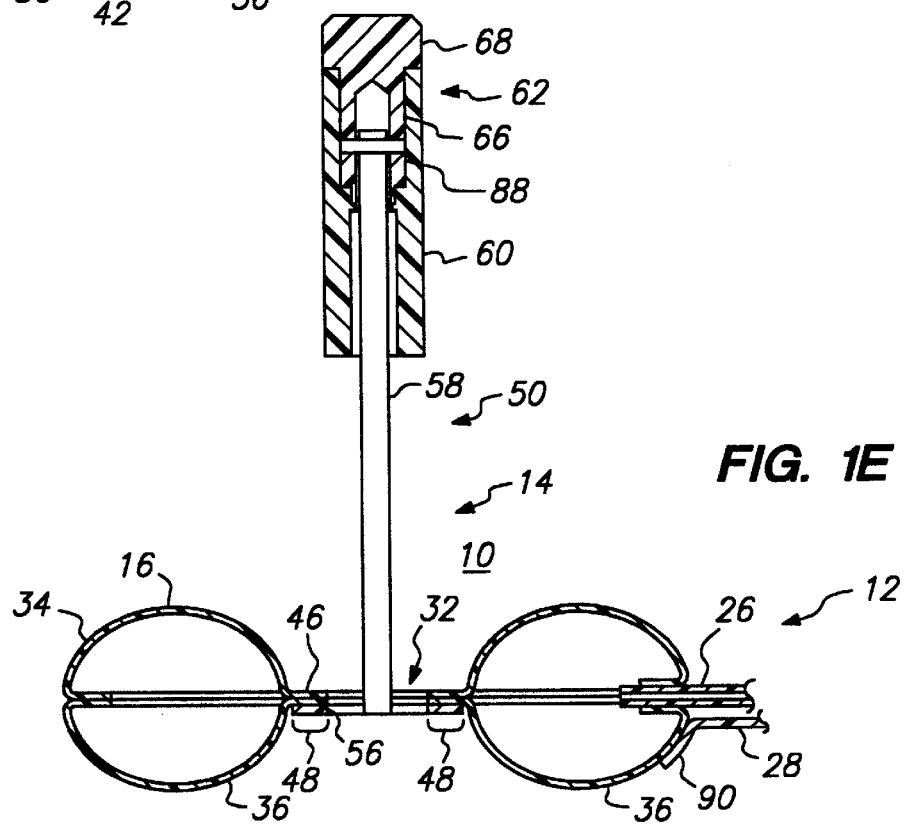
FIG. 1E is a second cross-sectional view, orthogonal to the first cross-sectional view, of the preferred embodiment of the lifting apparatus according to the invention in its inflated state.

It is therefore preferred to connect the upper envelope half 34 to the lower envelope half 36 in the manner shown in FIGS. 1D and 1E. In this embodiment, the outer seam 42 is contained by the body wall engaging element 12, and the envelope 18 isolates the outer seam 42 from the patient. Consequently, no additional processing is required to provide a smooth outer edge to the outer seam. The outer seam 42 is formed inside the body wall engaging element 12 by a two-step welding process in which the upper envelope half 34 is welded to the lower envelope half 36 at the outer seam 42 first, and the resulting structure is turned inside out before the upper envelope half 34 is welded to the lower envelope half 36 at the inside seam 38.

Locating the outer seam 42 inside the body wall engaging element 12 imposes an additional requirement on the envelope material. The exposed ends of the threads of the nylon fabric inside the body wall engaging element 12 are exposed to the inflation fluid at the inflation pressure, whereas the ends of these threads adjacent the inner seam 38 are exposed to the ambient pressure of the body cavity. The threads are porous, and the pressure differential between the ends of the threads causes inflation fluid to leak from the body wall engaging element along the length of the threads. To prevent this leakage of inflation fluid, the nylon fabric is made non-porous by saturating it with polyurethane prior to laminating it between the polyurethane films.

A small section 43 of the outer seam 42 in the body wall engaging element 12 shown in FIGS. 1A–1F, and a small section of the outer seam 40 in the body wall engaging element 12A shown in FIGS. 3A and 3B is left unwelded to provide a gap into which the inflation tube 26 is inserted, as will be described in detail below.

Localized stress in the body wall engaging element 12 is minimized by the lifting element 14 applying the lifting force to a relatively large an area of the body wall engaging element. Minimizing localized stress increases the safety margin between the maximum stress in the body wall engaging element and material strength and the weld strength of the envelope halves 34 and 36 of the body wall engaging element. On the other hand, it is desirable that the lifting element 14 not extend beyond the dimensions of the incision in the direction perpendicular to the lifting direction. In the lifting apparatus according to the invention, these conflicting requirements are met by making the central hole 32 relatively large (about one inch (25 mm) in diameter), and configuring the lifting element 14 to apply the lifting force to the equator 46 of body wall engaging element 12. The large diameter of the central hole 32 has the added advantage of providing greater ease of access to the working space for surgical instruments passed though the incision.

The body wall engaging element 12 is adapted for receiving the lifting force at its equator 46 by increasing the width of the inner seam 38 beyond that which is required to reliably join the upper envelope half 34 to the lower envelope half 36. The extended-width inner seam provides the lifting flange 48. In the preferred embodiment, the lifting flange is about 0.25" (6 mm) wide.

The flexible lifting element 14 is composed of the flexible element 50 and the arm attachment element 52. The arm attachment element is configured for attachment to a table-mounted standard lifting arm, such as the Laparolift™ sold by the assignee of the present invention, and for transferring the lifting force exerted by the lifting arm to the flexible element 50. The flexible element, in turn, transfers the lifting force from the arm attachment element 52 to the body wall engaging element 12, to which the flexible element is attached.

The flexible element 50 has a number of practical advantages over the rigid lifting tube of the inflating lifting apparatus described in the prior application. The flexible element reduces the bulk of the lifting apparatus in the form in which it is inserted into and removed from the body cavity. The flexible element minimally obstructs the movement of instruments inserted into the incision. If the surgeon desires to move an instrument to a position where it would be obstructed by the flexible element, he/she can simply move the flexible element out of the way. The flexible element allows the patient to move or be moved laterally relative to the lifting arm. Finally, the flexible element enables the body wall engaging element 12 to be operated at different angles relative to the direction of the lifting force exerted by the lifting arm.

The flexible element 50 must transfer a lifting force of up to 40 pounds (180 N) to the lifting flange 48 on the equator 46 of the body wall engaging element 12 in a manner that minimizes localized stress. The preferred embodiment of the flexible element 50, called the epsilon 54, is shown in FIG. 4A. The epsilon 54 distributes the lifting force substantially uniformly over the entire area of the lifting flange.

The epsilon 54 is cut from a single piece of composite material and consists of two semi-annular portions 56 integral with, and interconnected by, the strap 58. The semi-annular portions are dimensioned such that they collectively cover substantially the entire area of the lifting flange 48, as shown in FIG. 1B. The epsilon 54 is preferably cut from a single piece of composite material using laser cutting or ultrasonic cutting. Both of these methods result in a clean edge that is protected from fraying by melting of the composite material during the cutting process.

A polyurethane film/nylon fabric composite, different from the envelope material, is used as the material for the epsilon 54. In the preferred embodiment, the fabric is formed from 840 denier spun nylon thread with 32×30 threads per inch. The fabric is treated with an anti-fraying resin, and is then laminated between two 5 mil. (125 μm) thick polyurethane films, to provide a material with a total nominal thickness of 24 mil. (600 μm). The thread orientation in the epsilon 54 is shown by the area 55 in FIG. 4A.

The nylon fabric in the composite material of the epsilon 54 is tightly woven to maximize the efficiency by which the lifting force applied to the strap 58 is distributed uniformly across the surface of the semi-annular portions 56. The lifting force is applied in the strap 58 to the relatively few warp threads 57 that run along the length of the strap from one of the annular portions 56 to the other. In the semi-annular portions, these warp threads transfer the lifting force to the relatively few weft threads 58 that are woven with them. These weft threads in turn distribute the lifting force to the threads covering the remainder of the area of the semi-annular portions.

The strap 58 is preferably made as long as possible to make the part of the strap attached to each of the semi-annular portions 56 as close to parallel as possible during lifting. This reduces the lateral component of the lifting force applied to opposite sides of the central hole 32 and the tendency of this lateral component to close the central hole. The length of the strap is limited in practice to about 13" (330 mm) by the maximum upwards excursion of the lifting arm. The strap is about 0.25" (6 mm) wide.

The semi-annular portions 56 are RF welded to the entire lifting flange area of the lower envelope half 36, preferably before the lower envelope half is welded to the upper envelope half 34. The lifting flange area of the lower envelope half is the part of the lower envelope half that will constitute the lifting flange 48 when the lower envelope half is welded to the upper envelope half 34. The semi-annular portions are welded over their entire area, so that, in the finished body wall engaging element, the lifting force is distributed over the entire area of the lifting flange 48, thereby minimizing localized stress.

The arm attachment element 52 is shown in detail in FIG. 5, and has three main components, the housing 60, the strap hanger 62, and the dovetail connector 64. The dovetail connector 64 is preferably molded integrally with the housing 60, and mates with a complementary dovetail connector (not shown) mounted on the lifting arm. The housing and the strap hanger are preferably moldings of a suitable plastic, for example, polycarbonate.

The dovetail connector 64, when mated with a complementary dovetail connector, transmits the lifting force unidirectionally, i.e., upwards. Also, because the dovetail connector 64 is off-center relative to the housing 60, it also transmits a torque to the complementary dovetail connector. If the lifting arm is lowered to a point at which the lifting force would be applied to the housing in a downwards direction, the dovetail connector automatically disengages from the complementary dovetail connector. This prevents the downwards force being transmitted via the housing to the patient. With the lifting apparatus according to the present invention, the flexible element 50 provides the main mechanism for minimizing the possibility of a downwards force being transmitted to the patient, and the dovetail connector 64 simply provides a backup.

The strap hanger 62 includes the cylindrical portion 66 extending axially from the center of the knob 68. The cylindrical portion is swivellingly received in the bore 70 of the housing 60. Rotating the knob 68 changes the rotational position of the strap 58 when the housing is attached to the table-mounted lifting arm. The upper rim 72 of the housing 60 transmits the lifting force to the lower face 74 of the knob 68 of the strap hanger 62. The cylindrical portion of the strap hanger 62 is formed with the groove 76 that engages with the flange 78 molded in the bore 70 of the housing to locate the strap hanger axially.

The cylindrical portion 66 of the strap hanger includes the axial bore 84, and the transverse bore 86 through the wall of the axial bore. The strap 58 is attached to the arm attachment element by forming the strap into a loop, inserting the loop into the axial bore 84 and inserting the pin 88 into the transverse bore 86 and the loop.

Returning now to FIGS. 1A and 1B, the inflation tube 26 is preferably a piece of polyurethane tube with an outside diameter of about 0.16" (4 mm) and a wall thickness of about 40 mil. (1 mm), about 15" (380 mm) long. The inflation tube is glued into the gap 43 between the envelope halves 34 and 36 left unwelded when the outer seam 42 was welded. A UW-cured cyano-acrylate adhesive is preferably used.

Kinking of the inflation tube 26 when the packaged body wall engaging element 24 is deployed inside a body cavity is prevented by fitting the inflation tube with the anti-kinking device 27 shown in FIGS. 1G and 1H. The anti-kinking device 27 is formed from a piece of 50-pound test monofilament about four inches (100 mm) long. The piece of monofilament is bent in half along its length and is inserted into the inflation tube close to where the inflation tube is connected to the envelope halves 34 and 36. Anti-kinking measures can be applied over a greater extend to the inflation tube 26 if necessary. Alternatively, kink-resistant tubing can be used for the inflation tube 26.

The inflation tube 26 is fitted at its end remote from the body wall engaging element 12 with the one-way valve 80. The valve 80 includes the portion 82 to which the bulb inflator 163 can be attached to inflate or evacuate the body wall engaging element. The valve 80 is a one-way valve and also preferably has a pressure-limiting characteristic. The pressure limiting characteristic of the valve 80 prevents the inflation pressure of the body wall engaging element from rising above a predetermined limit pressure. The limit pressure of the valve 80 is chosen to be greater than the minimum pressure required to provide the body wall engaging element 12 with the stiffness it requires to enable it to transfer the lifting force to the body wall, but well below the pressure at which the integrity of the body wall engaging element is impaired. In the preferred embodiment, the limit pressure is chosen to be 10 psi (70 kPa).

The pressure limiting characteristic of the valve 80 enables the surgeon to inflate the body wall engaging element without having to monitor the inflation pressure and without having to be concerned about over-inflating the body wall engaging element. The surgeon simply operates the bulb inflator 163 until he/she hears air being released by the valve 80, which indicates that the pressure in the body wall engaging element has reached the operating pressure. If the procedure is lengthy, the bulb inflator can be operated occasionally to replace inflation fluid lost due to minor leakage. The bulb inflator is again operated until the valve 80 is heard to release.

The valve 80 can alternatively and preferably simply have a one-way characteristic, and the bulb inflator 163 can be fitted with the pressure-limiting valve 164. The pressure limiting valve 164 fitted to the bulb inflator limits the inflation pressure of the body wall engaging element similarly to the valve 80 with a pressure limiting characteristic. References hereinafter to the valve 80 having a pressure limiting characteristic will be understood to include a valve with a pressure limiting characteristic included into the bulb inflator.

The tether 28 shown in FIG. 4B provides a reliable means for withdrawing the collapsed body wall engaging element 12 from the body cavity at the end of the procedure. The distal end 90 of the tether is attached to one of the envelope halves, preferably the lower envelope half 36, close to the outer seam 42 at or close to the point on the periphery of the envelope half to which the inflation tube 26 will later be attached. Prior to attaching the end of the tether 28 to the envelope half, the tether is oriented so that it extends radially outwards from the center of the envelope half. The tether is preferably attached to the lower envelope half by RF welding before the lower envelope half is welded to the upper envelope half 34.

The tether 28 is cut from a piece of the same type of composite material as the epsilon 54. The warp threads of the fabric core of the composite material are oriented along the length of the tether, as shown by the area 93 in FIG. 4B.

When the packaged body wall engaging element 24 is inserted into the body cavity at the beginning of the procedure, tether 28 extends from the proximal end of the package. After the body wall engaging element has been inserted into the body cavity, the proximal end 92 of the tether remains outside the body cavity. At the end of the procedure, following deflation and evacuation of the body wall engaging element 12 to a collapsed state, the proximal end 92 of the tether is pulled proximally to withdraw the collapsed body wall engaging element edge-first from the body cavity through the incision.

Withdrawing the collapsed body wall engaging element edge-first requires a relatively moderate force of about 10 pounds (45 N). The collapsed body wall engaging element 12 could alternatively be withdrawn center-first by pulling on the lifting element 14, but this would require a much greater force (30–40 pounds (135–180 N)). The inflation tube 26 may be pulled proximally to assist the tether 28 in withdrawing the collapsed body wall engaging element from the body cavity, but it is impractical to use the inflation tube as a substitute for the tether. The inflation tube itself is too elastic, and the strength of the glued joint between the inflation tube and the envelope 18 is insufficient for the inflation tube to serve as a reliable substitute for the tether.

The lifting apparatus 10 is shown in its packaged state, prior to insertion into the body cavity in FIG. 2A. A cross-sectional view of the packaged body wall engaging element 12 is shown in FIG. 2B, and an enlarged cross-sectional view of the packaged body wall engaging element 12 is shown in FIG. 2C. The body wall engaging element 12 is packaged in a manner that minimizes the cross-sectional area of the package 24. Tis minimizes the size of the incision required for the body wall engaging element to be inserted into the body cavity, and, hence, minimizes trauma to the patient. The body wall engaging element 12 is also packaged in a manner that enables the body wall engaging element to be released from its packaging simply by inflating the body wall engaging element, and that enables withdrawal of the body wall engaging element from the body cavity automatically to withdraw the packaging.

The body wall engaging element 12 is maintained in its packaged state by the pouch 22. The pouch is made by attaching the upper pouch half 94 to the lower pouch half 96 along their peripheries at their sides 98 and distal end 105.

This leaves the proximal end 101 open. The upper and lower pouch halves are preferably attached to one another by RF welding. The upper and lower pouch halves are cut from a thin film of a weldable plastic, such as 2 mil. (80 $\mu$m) polyurethane. The length of the pouch halves is about one inch (25 mm) greater than the diameter of the upper and lower envelope halves 34 and 36.

The upper pouch half 94 bounds the aperture 29 through which the flexible element 50 exits the pouch 24. The lower pouch half 96 includes the line of perforations 103 formed along part of its center line, preferably in the same operation in which the lower pouch half is cut from the film of weldable plastic. The line of perforations 103 extends proximally along the length of the lower pouch half from the distal end 105 to the terminator 107, which is spaced about ½" (12 mm) from the open proximal end 101. The terminator 107 is a small circular aperture about 60 mil. (240 microns) in diameter, and serves to define the proximal end of the line of perforations. The function of the terminator 107 will be described in more detail below.

To package the body wall engaging element 12, the body wall engaging element is first evacuated to prevent air trapped inside the body wall engaging element from increasing the bulk of the package. Evacuation reduces the body wall engaging element 12 to a substantially flat disc. The flexible lifting element 14 is arranged to extend from the upper envelope half 34 side of the body wall engaging element, i.e., to extend from the side of the body wall engaging element from which will extend in use. The inflation tube 26 and the tether 28 are arranged to extend radially from the body wall engaging element 12.

Opposite ends 113 of the diameter of the envelope 18 perpendicular to the direction of the inflation tube 26 and the tether 28 are then rolled in the direction shown by the arrows 115 in FIG. 1C. This direction is opposite to that from which the flexible lifting element 14 extends from the body wall engaging element 12. This rolls the opposite ends 113 of the diameter of the envelope 18 inwards towards the central hole 32. Rolling is continued until the two rolled portions of the envelope contact one another, as shown in FIGS. 2B and 2C. As the rolled portions of the envelope approach the center of the body wall engaging element, the semi-annular portions 56 of the epsilon 54 are also subject to rolling. Since the epsilon 54 is flexible, the semi-annular portions 56 easily conform to the shape of the rolled envelope portions, and do not distort the shape of the package 24. When fully rolled, the body wall engaging element 12 is substantially cylindrical, and has the inflation tube 26 and the tether 28 extending from its proximal end, and has the flexible lifting element 14 extending from its center.

The body wall engaging element 12 is held in its rolled state, and the arm attachment element 52 of the flexible lifting element 14 is threaded through the pouch 22, entering at the open proximal end 101 and leaving through the aperture 29, drawing the strap 58 behind it. This orients the rolled body wall engaging element relative to the pouch so that the rolled portions of the envelope face towards the line of perforations 103 in the lower pouch half 96. The distal end of the rolled body wall engaging element 12, remote from the inflation tube 26, is then inserted into the pouch 22 through the open end 101. As the rolled body wall engaging element is inserted, the arm attachment element 52 is pulled axially to withdraw the strap 58 from the pouch.

Insertion is continued until the distal end of the rolled body wall engaging element reaches the distal end 105 of the pouch. The arm attachment element 52 is then manipulated to lay the strap 58 along the length of the package 24, and to bring the arm attachment element close to the inflation tube 26 and the tether 28 emerging from the open end 101 of the pouch 22, as shown in FIG. 2A. An enlarged cross sectional view of the rolled body wall engaging element 12 inside the pouch 22 is shown in FIG. 2C. To prevent tangling, the inflation tube 26 and the tether 28 may temporarily be attached to the arm attachment element 52 following manufacture and prior to use.

Rolling the body wall engaging element 12 and inserting the body wall engaging element into the pouch 22 with the lifting element emerging from the aperture 29, and with the rolled portion facing the line of perforations 103 enables the pouch to reliably retain the rolled body wall engaging element in its rolled state during storage and insertion of the body wall engaging element into the body cavity, and yet enables inflation of the body wall engaging element to release the body wall engaging element from the pouch. Initial inflation of the rolled body wall engaging element 12 causes the rolled body wall engaging element to unroll slightly. This applies a lateral stress to the lower pouch half 96, which causes the lower pouch half to split along the line of perforations 103. The lower pouch half splitting releases the pouch from around the rolled body wall engaging element, and allows the body wall engaging element to expand unimpeded by the pouch.

The terminator 107 at the proximal end of the line of perforations 103 reduces the tendency for the lower pouch half to tear beyond the end of the line of perforations when the body wall engaging element 12 is inflated. As a result, the part 111 of the pouch encircling the inflation tube 26 and the tether 28 remains intact and keeps the pouch connected to the body wall engaging element following release of the body wall engaging element from the pouch 22. The pouch is additionally connected to the body wall engaging element by the strap 58 passing through the aperture 29 in the pouch. These connections between the pouch and the body wall engaging element following release of the body wall engaging element from the pouch enable removal of the body wall engaging element from the body cavity at the end of the procedure to automatically remove the pouch from the body cavity.

A method according to the invention of using the lifting apparatus according to the invention win be described below.

Figure 6A:
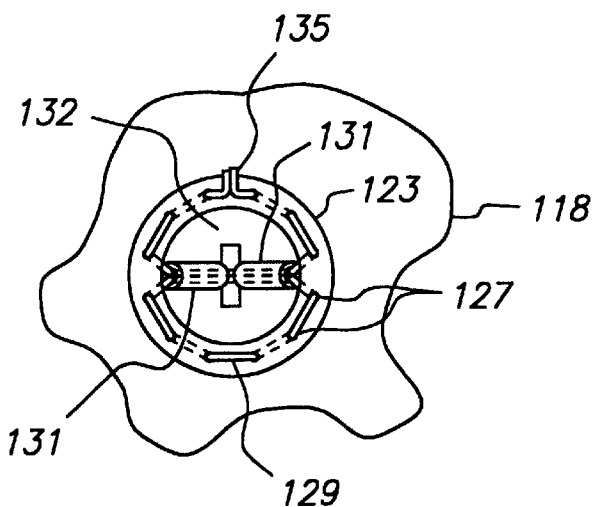
FIGS. 6A, 6B, and 6C are respectively a bottom view, a vertical cross-sectional view and a side view of a first alternative embodiment of the flexible lifting element according to the invention.
Figure 6B:
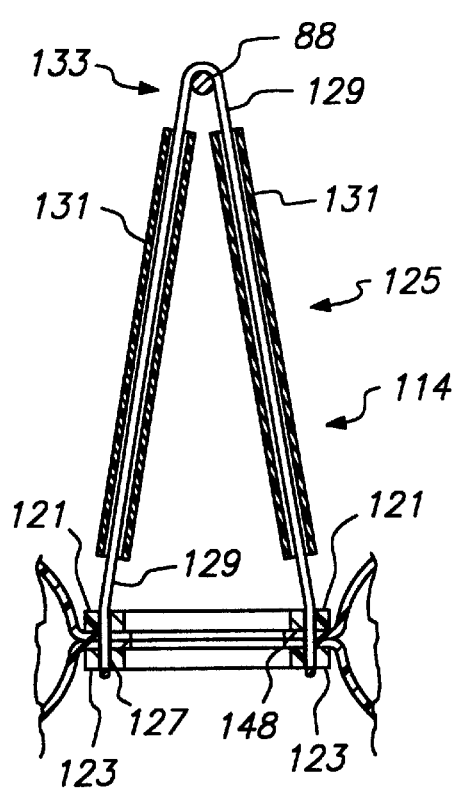
Figure 6C:
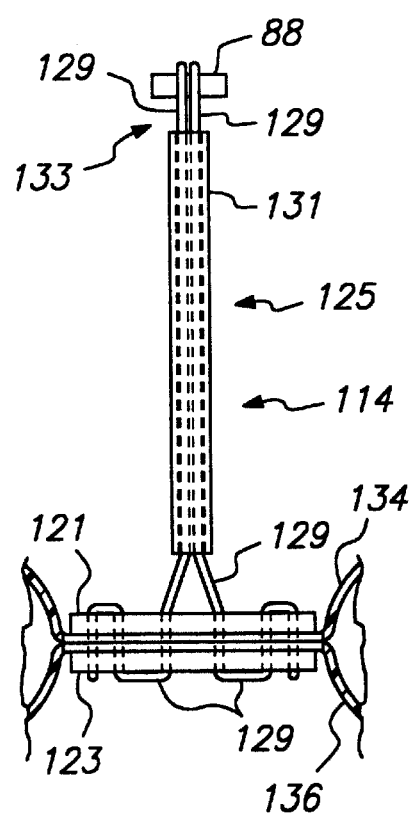

Parts of an alternative embodiment 110 of the lifting apparatus according to the invention are shown in FIGS. 6A–6C. In the embodiment shown in FIGS. 6A–6C, elements that are the same as those shown in FIGS. 1A–1F are indicated by the same reference numerals, and elements that are similar to those shown in FIGS. 1A–1F are indicated by the same reference numerals with 100 added. In FIG. 6, the part of the envelope 118 of the body wall engaging element 112 that forms the lifting flange 148 is pierced with the punctures 119. The punctures are located at substantially constant angular intervals and are inset from the inner perimeter of the lifting flange.

The embodiment shown in FIGS. 6A–6C has a different flexible lifting element from the embodiment shown in FIGS. 1A–1F. The flexible lifting element 114 shown in FIGS. 6A–6C includes the upper ring 121, the lower ring 123, and the suspension 125.

The lifting flange 148 of the body wall engaging element 112 is sandwiched between the upper ring 121 and the lower ring 123. The upper ring and lower ring are similar to one another and are circular with a rectangular or square cross section. The upper ring and lower ring are preferably moldings of a rigid plastic such as a polyetherimid. The upper ring 121 and the lower ring 123 are formed with the holes 127 (one of twelve holes is indicated by the reference numeral 127 in FIG. 6A) corresponding to the punctures 119 in the lifting flange 148. Because the upper ring and the lower ring are rigid, they define a minimum cross-sectional dimension for the packaged apparatus. In a version of the lifting apparatus capable of being inserted through an incision about 14 mm long, the outside diameter of the upper and lower rings is about 0.75" (19 mm). The inner diameter of the upper and lower rings defines the central hole 132, and is about 0.5" (12 mm). This is smaller than the one-inch (25 mm) diameter of the central hole 32 of the embodiment shown in FIGS. 1A–1F.

The upper ring 121A and the lower ring 123A can be elliptical instead of circular. In this case, the upper ring and the lower ring are preferably aligned with their major axes in the direction of the inflation tube 26 and the tether 28. This aligns the minor axes of the rings perpendicular to the longitudinal axis of rolled body wall engaging element, and provides the central hole with an increased area compared with circular upper and lower rings without increasing the cross-sectional area of the body wall engaging element 112 in its packaged state.

The monofilament 129 and the sleeves 131 form the suspension 125. The monofilament 129 is a length of 50-pound test nylon monofilament about 20 mil. (0.5 mm) in diameter, and the sleeves are each a length of polyurethane or PVC tubing with an internal diameter of 40 mil. (1 mm), an outside diameter of 80 mil. (2 mm), and a length of over twice that of the strap 58. The sleeves serve as a cushion between the monofilament 129 and the incision, and prevent the monofilament from enlarging the incision.

The monofilament 129 is sequentially threaded through the holes 127 in the upper and lower rings 121 and 123 and the corresponding punctures 119 in the lifting flange 148, and is threaded twice through each sleeve 131, as shown in FIGS. 6A–6C. Finally, the free ends of the monofilament 129 emerge in the same direction from two adjacent ones of the holes 127 in the lower ring 123 and are connected together as indicated by the reference numeral 135. This attaches the upper ring 121 and the lower ring 123 to opposite sides of the lifting flange 148, and forms the suspension 125.

The suspension 125 is connected in the arm attachment element 52 (omitted from the drawings for clarity) by forming the portions 133 of the monofilament 129 remote from the upper ring 141 into a loop, inserting the loop into the axial bore 84 of the strap hanger 62 and inserting the pin 88 into the transverse bore 86 and the loop in a manner similar to that shown in FIG. 5.

Alternatively, the upper ring 121 can be attached to the lower ring 123 and the lifting flange 148 by riveting through all but two pairs of diametrically-opposite ones of the holes 127. The monofilament 129 can then be threaded through each of the non-riveted holes and the sleeves 131 to form the suspension 125.

Figure 7A:
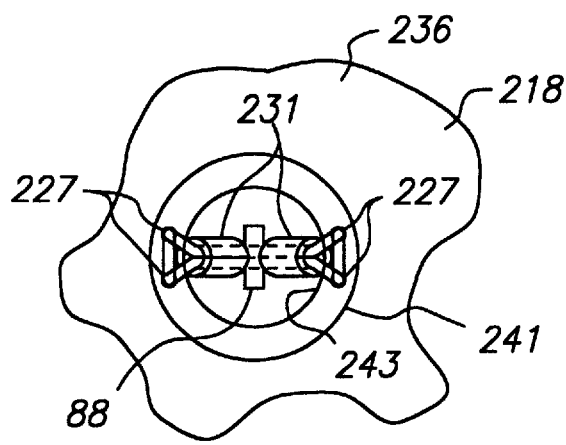
FIGS. 7A, 7B, and 7C are respectively a bottom view, a vertical cross-sectional view and a side view of a second alternative embodiment of the flexible lifting element according to the invention.
Figure 7B:
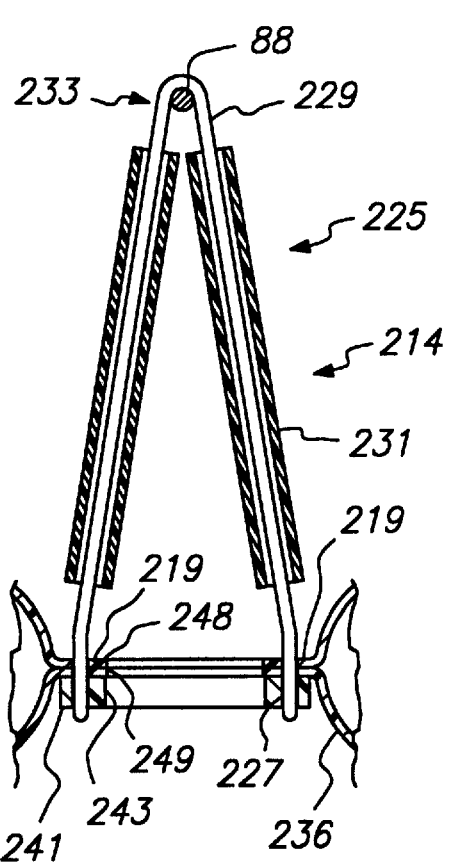
Figure 7C:
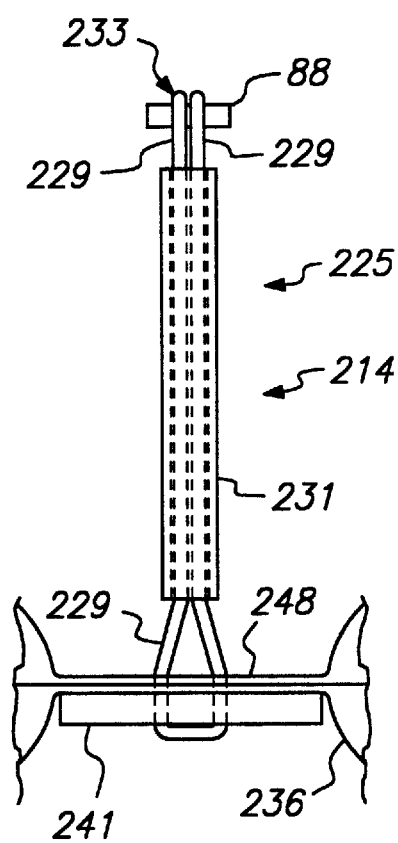

Part of another alternative embodiment 210 of the lifting apparatus according to the invention is shown in FIGS. 7A–7C. In the embodiment shown in FIGS. 7A–7C, elements that are the same as those shown in FIGS. 1A–1F are indicated by the same reference numerals, and elements that are similar to those shown in FIGS. 1A–1F are indicated by the same reference numerals with 200 added. In FIGS. 7A–7C, the part of the envelope 218 (only a part of the envelope is shown) of the body wall engaging element that forms the lifting flange 248 is pierced with the two pairs of diametrically-opposite punctures 219. The punctures are inset from the inner perimeter 249 of the lifting flange 248.

The embodiment shown in FIGS. 7A–7C has a different flexible lifting element from the embodiments shown in FIGS. 1A–1F and in FIGS. 6A–6C. The flexible lifting element 214 shown in FIGS. 7A–7C includes the ring 241 and the suspension 225.

The ring 241 is circular with a rectangular cross section and is cut from a nylon fabric/polyurethane composite material similar to the envelope material, but of considerably greater thickness (about 2.5 mm (0.1")). The ring 241 is formed with the diametrically-opposed pairs of holes 227 corresponding to diametrically-opposed punctures 219 in the lifting flange 248. The ring 241 is attached to the portion of the lower envelope half 236 forming the lifting flange 248, preferably by RF welding, with the holes 227 aligned with the punctures 219. In a version of the lifting apparatus capable of being inserted through an incision about 14 mm long, the outside diameter of the ring 241 is about one inch (25 mm), and its inside diameter, which defines the central hole 232, is about 0.5" (12 mm). This is smaller than the one-inch diameter of the central hole 32 of the embodiment shown in FIGS. 1A–1F.

A piece of very high-strength nylon string 229 enclosed by the sleeve 231 provides the suspension 225. The nylon string is looped through the pairs of diametrically-opposed holes 227 and threaded twice through the sleeve 231, as shown in FIGS. 7B and 7C, and its free ends are connected together. The sleeve 231 retains any fibres shed from the nylon string 229. Alternatively, nylon monofilament or stainless-steel wire string may be used, in which case the sleeve prevents the monofilament or the wire from enlarging the incision.

The suspension 225 is connected in the arm attachment element 52 (omitted from the drawings for clarity) by forming the portions 233 of the string 229 remote from the ring 241 into a loop, inserting the loop into the axial bore 84 of the strap hanger 62 and inserting the pin 88 into the transverse bore 86 and the loop in a manner similar to that shown in FIG. 5.

Figure 8A:
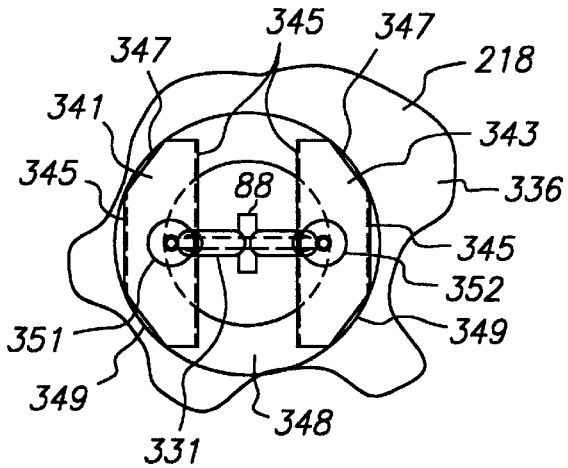
FIGS. 8A, 8B, and 8C are respectively a bottom view, a vertical cross-sectional view and a side view of a third alternative embodiment of the flexible lifting element according to the invention.
Figure 8B:
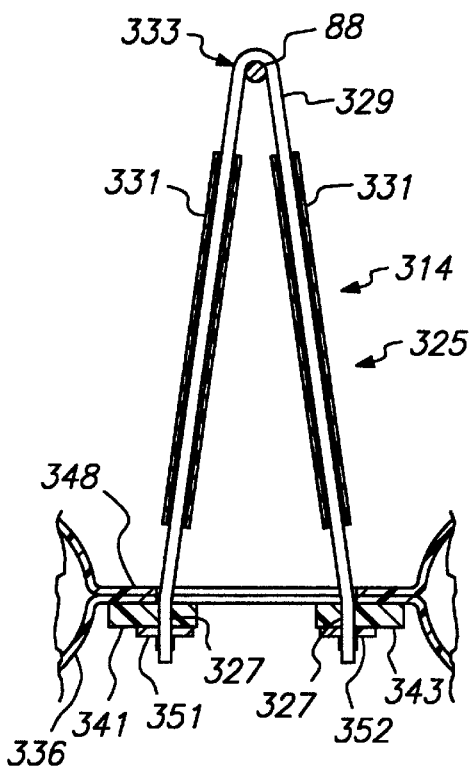
Figure 8C:
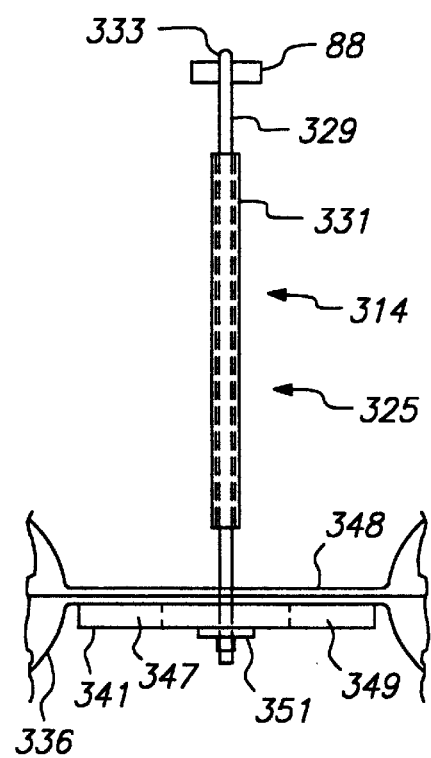

Part of another alternative embodiment 310 of the lifting apparatus according to the invention is shown in FIGS. 8A–8C. In the embodiment shown in FIGS. 8A–8C, elements that are the same as those shown in FIGS. 1A–1F are indicated by the same reference numerals, and elements that are similar to those shown in FIGS. 1A–1F are indicated by the same reference numerals with 300 added. In FIGS. 8A–8C, the body wall engaging element is the same as that shown in FIGS. 1A–1F, but the flexible lifting element 314 is different from that of the embodiments shown in FIGS. 1A–1F, FIGS. 6A–6C, and FIGS. 7A–7C is used. The flexible lifting element 314 shown in FIGS. 8A–8C includes the transfer segments 341 and 343 and the suspension 325.

In the embodiment shown in FIGS. 7A–7C, the ring 241 is cut from a piece of fabric-reinforced composite material. The ring made this way has an unfinished inside edge 243 (FIGS. 7A and 7B) that has a relatively low resistance to lateral tearing. Hence, the ring must be made strong enough to prevent the lifting force from causing the nylon string to tear the ring from the holes 227 to the inside edge 243. Consequently, the suspension 225 in the embodiment shown in FIGS. 7A–7C is formed by looping the nylon string 229 through two holes on each side of the ring 241 to reduce the lateral pressure between the nylon string and the holes 227.

The reduced lateral pressure reduces the ability of the nylon string to tear the ring 241. The ring 241 is also formed using a thick (2.5 mm) composite material to reduce its resistance to tearing.

In the embodiment shown in FIGS. 8A–8C, the transfer segments 341 and 343 are short lengths of a ribbon of a nylon fabric/polyurethane composite material similar to the envelope material. The thickness of this material is about 1.2 mm, which is considerably greater than that of the envelope material, but less than the composite material used to form the ring 241 in the embodiment shown in FIGS. 7A–7C. The ribbon is woven with selvedges, indicated by the broken lines 345, along its length. A selvedge is about twenty times more resistant to lateral tearing than the unfinished inside edge 243 of the ring 241 in the FIGS. 7A–7C embodiment. Each transfer segment is cut from the ribbon with the portions 347 and 349 shaped to match the outer perimeter of the lifting flange. This enables the transfer segments to seat flat on the lifting flange 348. In a version of the lifting apparatus capable of being inserted through an incision about 14 mm long, the transfer segments are about 15 mm wide and 40 mm long. Each of the transfer segments 341 and 342 is formed with the hole 327. In the example shown, the hole is formed in a portion of the transfer segment that does not overlap the lifting flange 348. No punctures need therefore be formed in the lifting flange. The transfer segments 341 and 343 are attached to the part of the lower envelope half 336 forming the lifting flange, preferably by RF welding. Prior to welding, the transfer segments are aligned so that their longitudinal axes are parallel to the direction of the lifting tube 26 (FIGS. 1A–1F). Thus, when the body wall engaging element is packaged, the transfer segments are rolled across their short dimensions.

A piece of very high-strength nylon string 329 enclosed by the sleeve 331 provides the suspension 325. The nylon string is threaded through one of the diametrically-opposed holes 327, through the sleeves 331, and the other of the diametrically-opposed holes 327. The ends of the nylon string are then respectively inserted into the flanged fittings 351 and 352, where they are retained by crimping the flanged fittings. The flanged fittings couple the lifting force to the transfer segments 341 and 343. Alternatively, the flanged fittings may be dispensed with, and the ends of the nylon string 339 may simply be knotted. A metal or plastic washer may be put on each end of the nylon string prior to knotting the ends of the string to distribute the lifting force over a wider area of the transfer segments. The flanged fittings also distribute the lifting force over a relatively large area of the transfer segments.

The suspension 325 is connected in the arm attachment element 52 (omitted from the drawings for clarity) by forming the portion 333 of the string 329 remote from the transfer segments 341 and 343 into a loop, inserting the loop into the axial bore 84 of the strap hanger 62 and inserting the pin 88 into the transverse bore 86 and the loop in a manner similar to that shown in FIG. 5.

The sleeve retains any fibres shed from the nylon string 329. Alternatively, nylon monofilament or stainless-steel wire string may be used, in which case the sleeve prevents the monofilament or the wire string from the enlarging the incision.

Figure 9A:
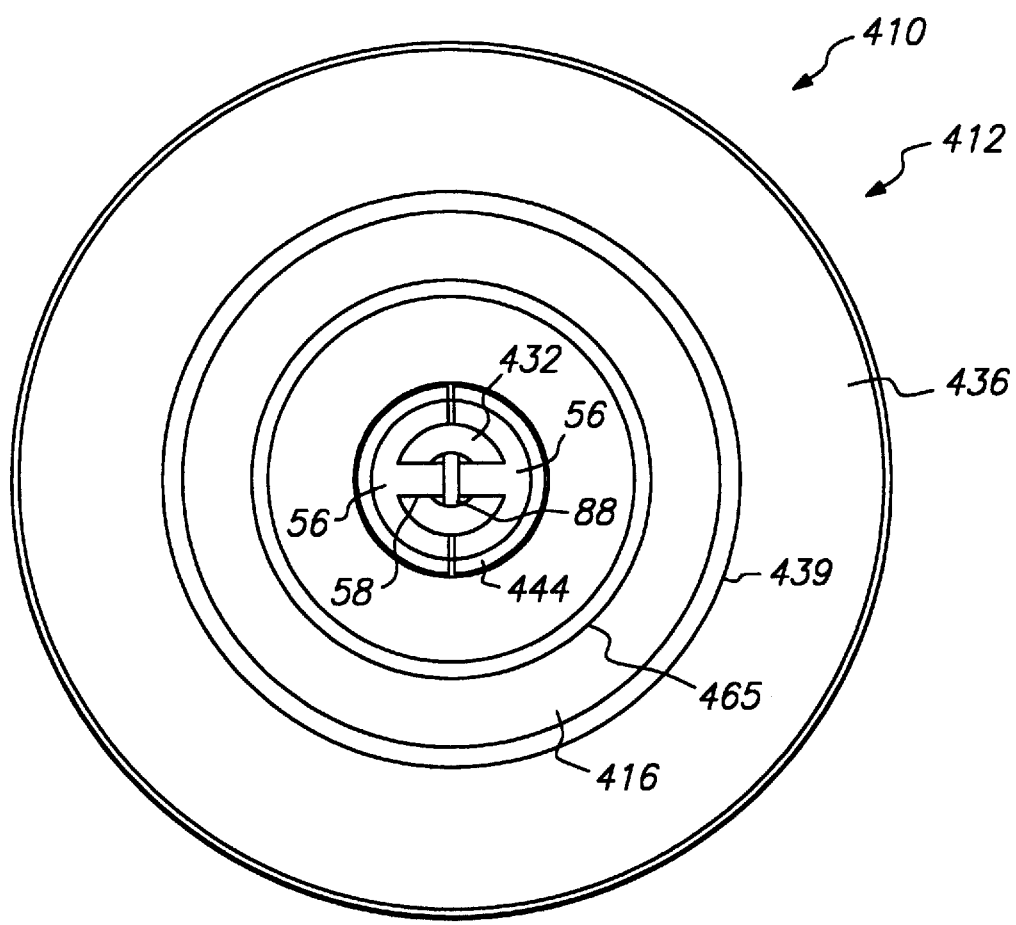
FIGS. 9A and 9B are respectively a bottom view and a vertical cross section of an embodiment of the lifting apparatus according to the invention with a second alternative embodiment of the body wall engaging element shown in its inflated state.
Figure 9B:
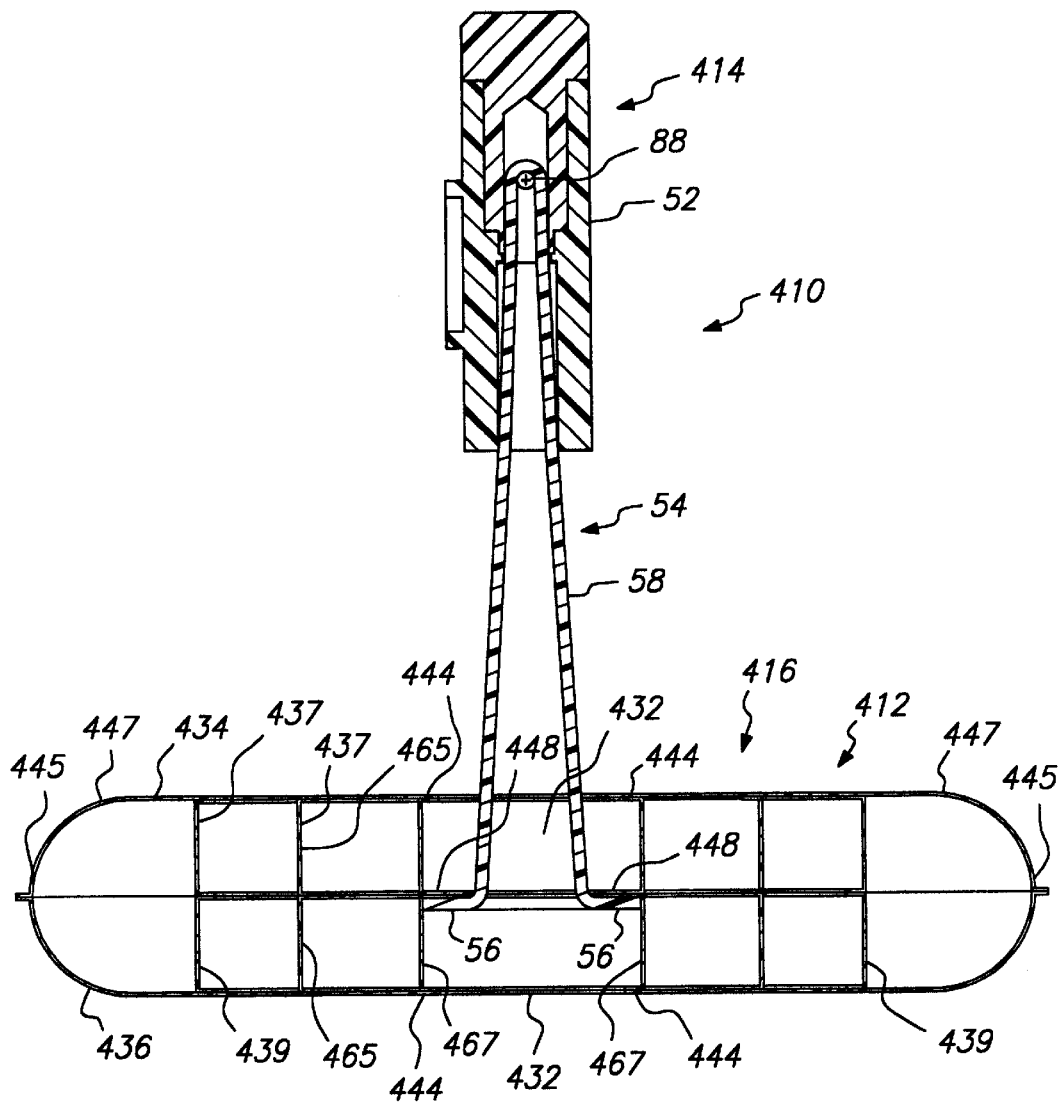

An alternative embodiment 412 of the body wall engaging element suitable for use with any of the flexible lifting elements 14, 114, 214, and 314 shown in FIGS. 1A–1F, 6A–6C, 7A–7C and 8A–8C is shown in FIGS. 9A and 9B. The embodiment of the body wall engaging element 412 shown in FIGS. 9A and 9B uses the flexible lifting element 14 shown in FIGS. 1A–1F as an example. The body wall engaging element 412 is based on the baffled body wall engaging element described in the prior application, but is adapted for connection to the flexible lifting element 14.

FIGS. 9A and 9B respectively show a bottom view and a cross-sectional view of the lifting apparatus 410 incorporating the alternative body wall engaging element 412 with the body wall engaging element in its inflated state. Prior to insertion into the body cavity, the body wall engaging element 412 is evacuated and packaged in a manner similar to that described above with reference to FIGS. 2A–2C. Accordingly, packaging the body wall engaging element 412 will not be described again here.

In its inflated state, the body wall engaging element 412 has the large, flat, lifting surface 416 by means of which it transfers the lifting force to the body wall. Despite the large area of the lifting surface, the height of the body wall engaging element in the axial direction is relatively small, typically in the range of 12–25 mm, which minimizes the intrusion of the inflated body wall engaging element into the working space created by lifting the body wall.

In this embodiment, the body wall engaging element 412 is substantially toroidal and bounds the central hole 32 that provides access to the tissues underlying the lifted body wall through the body wall engaging element. The large area of the lifting surface 416 of the body wall engaging element 412 enables a large area of the body wall to be lifted and distributes the lifting force applied to the flexible lifting element 414 uniformly over this large area. As a result, the maximum lifting pressure applied to the body wall is not significantly greater than that applied by convention gas insufflation.

The body wall engaging element 412 is formed from an upper envelope half 434 and a lower envelope half 436 which are joined together at their outer peripheries 445 and are interconnected at their inner peripheries 444 and at several intermediate points by the baffles 437. The inner-most baffle 465 bounds the central hole and is formed to include the lifting flange 448 to which the flexible lifting element 414 is attached. In the example shown, the semi-annular portions 56 of the epsilon 54 are welded to the underside of the lifting flange 448, and the strap 58 of the epsilon is connected to the arm attachment element 52 by the pin 88, as described above with reference to FIG. 5.

The upper envelope half 434 and the lower envelope half 436 form the envelope 418 of the body wall contacting element 412. The envelope halves are annular and are shaped to define the shape of the body wall engaging element and to define the extent of the central hole 432. In the circular body wall engaging element 412 shown in this example, the upper and lower envelope halves are substantially circular. The envelope halves are attached to one another at their outer peripheries 445, preferably by RF welding.

The baffles 437 interconnect the upper and lower envelope halves 434 and 436. The baffles provide the body wall engaging element 412 with its plane lifting surface 16 when the body wall engaging element is inflated. Without the baffles, the lifting surface would be convex, as in the embodiments shown in FIGS. 1A–1F. The inner-most baffle 467 connects the inner peripheries 444 of the upper and lower envelope halves and also provides the part of the body wall engaging element 412 that bounds the central hole 432.

The inner-most baffle 467 is formed in the same manner as the other baffles 437, as will be described in detail below. However, the upper and lower baffle halves constituting the inner-most baffle 467 are attached to one another over an extended area to form the lifting flange 448. The semi-annular portions 56 of the epsilon 54 are then attached to the part of the lower baffle half constituting the lifting flange. RF welding is the preferred way of attaching the upper and lower baffle halves to one another and to the semi-annular portions of the epsilon.

The position of the outer-most baffle 439 relative to the outer periphery 445 of the envelope halves is chosen to provide the body wall engaging element 412 with the rounded shoulder 447. The rounded shoulder helps the body wall engaging element conform to the shape assumed by the abdominal wall at the transition between the portion of the abdominal wall that supported by the inflating lifting apparatus and the portion that is not supported. This prevents the lifting pressure applied to the abdominal wall increasing at the periphery of the body wall engaging element.

When the body wall engaging element 412 is inflated to its inflated state, the baffles 437 provide the body wall engaging element with much of the stiffness by which the body wall engaging element uniformly transfers the lifting force from the flexible lifting element 414 to the large area of the body wall. The baffles are preferably attached to the envelope halves by RF welding, as will be described below.

In the preferred embodiment, the baffles 437 are arranged so that they run parallel to the outer periphery 445 of the body wall engaging element 412. This divides the body wall engaging element into a number of communicating concentric chambers. To allow inflation fluid to pass freely from the lifting tube 414 to each of the chambers, the holes 465 are formed in the baffles. In some applications, some of the baffles may be arranged radially.

The body wall engaging element 412 must be capable of withstanding inflation pressures sufficiently high to provide it with the stiffness necessary to transfer the lifting force uniformly from the flexible lifting element 414 to the body wall. On the other hand, to minimize the bulk of the body wall engaging element in its packaged state, and, hence, to minimize the size of incision required, as thin a material as possible should be used for the envelope halves 434 and 436 and the baffles 437. Also, because of the stresses imposed by the inflation pressure on the attachment points between the envelope halves and the between the envelope halves and the baffles, the material of the envelope halves and the baffles must have good welding characteristics. Because of these requirements, the envelope halves and the baffles are preferably made of a composite film made by laminating a material with good welding characteristics, such as urethane, with a strong material, such as polyester. An alternative composite material is a composite film made by extruding a material with good welding characteristics, such as polyethylene, with a strong material, such as nylon.

In the preferred embodiment, a nylon or polyester fabric layer about 0.5 to 2 mil. (12–50 $\mu$m) thick is used as the core of the envelope material. The nylon or polyester fabric layer can be a woven fabric or can be a layer of randomly-oriented fibres. The nylon or polyester fabric layer is laminated between two polyurethane films to provide a film of envelope material with a preferred thickness of about 3 mil. (75 $\mu$m). The polyurethane films bond securely to the uneven surface of the nylon or polyester fabric layer.

The baffles 437 are preferably fabricated and attached to the upper envelope half 434 and the lower envelope half 436 by the process shown in FIGS. 10A through 10E. This process assembles the baffles and attaches them to the upper and lower envelope halves using two welding operations. The two-piece baffle used in the procedure saves having to bend the baffles prior to welding, as would be required if one-piece baffles were used. In the following example, the assembly of the circular body wall engaging element 412 shown in FIGS. 1A–1D will be described.

Figure 10A:
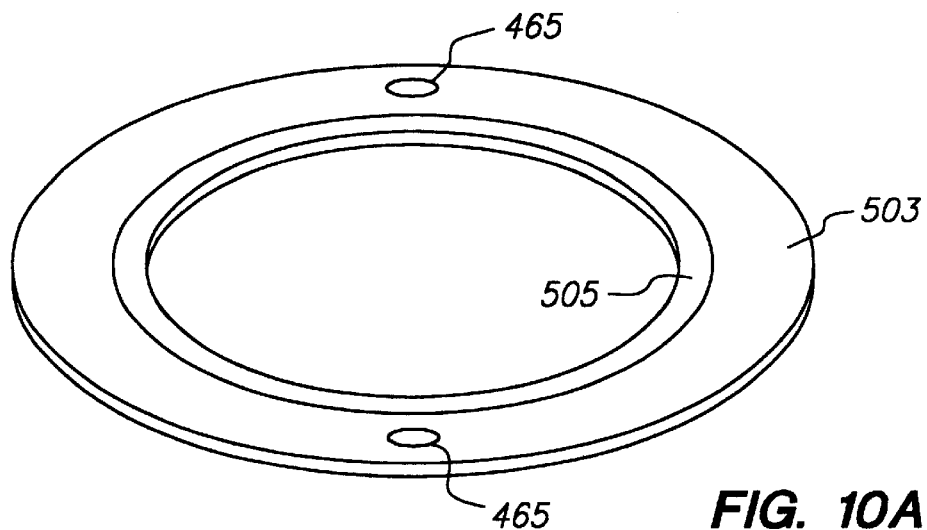
FIGS. 10A through 10E illustrate the process by which the baffles of the embodiment of the body wall engaging element shown in FIGS. 9A and 9B are formed and are attached to the upper and lower envelope halves by RF welding, and the process by which the lifting flange is formed in this embodiment.
Figure 10B:
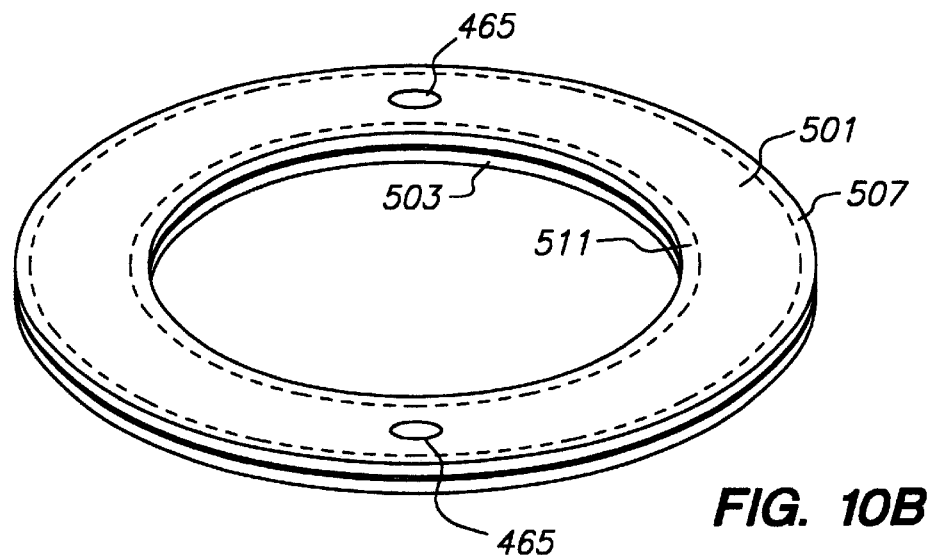
Figure 10C:
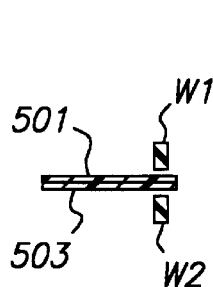

Each baffle is made from the annular upper baffle half 501 and the annular lower baffle half 503. One of the baffle halves, for example, the lower baffle half 503 is selectively coated with a suitable welding release agent in the shaded area 505 shown in FIG. 10A. The upper baffle half 501 is then laid on top of the lower baffle half 503, as shown in FIG. 10B, and the pair of baffle halves is placed between the first pair of circular RF welding electrodes $W_1$ and $W_2$, as shown in the cross-sectional view of FIG. 10C. The first welding electrodes $W_1$ and $W_2$ then weld the two baffle halves together along their outer peripheries, as indicated by the phantom line 507 shown in FIG. 10B, to form the baffle 437.

Figure 10D:
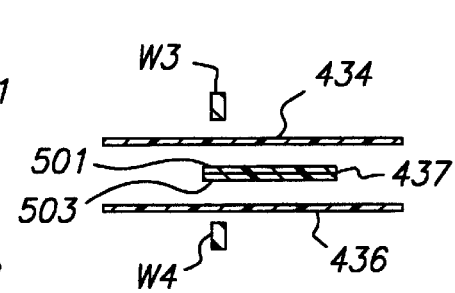
Figure 10E:
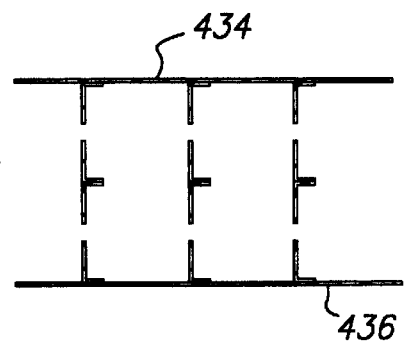

The completed baffle 437 is then laid on the lower envelope half 436 between the circular second welding electrodes $W_3$ and $W_4$, as shown in the cross-sectional view of FIG. 10D. The second welding electrodes have a smaller diameter than that of the first welding electrodes $W_1$ and $W_2$. The upper envelope half 434 is then laid over the completed baffle and the lower envelope half. The second welding electrodes $W_3$ and $W_4$ then perform a second welding operation to weld the baffle 437 along the inner periphery the baffle to the upper envelope half and the lower envelope half. For example, the second welding operation welds the upper baffle half 501 to the upper envelope half 434 along the phantom line 511, remote from the phantom line 507, shown in FIG. 10B.

The second welding operation welds the upper baffle half 501 to the upper envelope half 434, and welds the lower baffle half 503 to the lower envelope half 436. However, because of the welding release agent 505 between the two baffle halves in the region of the second weld, the second welding operation does not weld the baffle halves together. Accordingly, when the body wall engaging element is inflated, as shown in the cross-sectional view of FIG. 10E, part of the baffle welded to the lower envelope half 436 separates from the part of the baffle welded to the upper envelope half 434 until the baffles 437 are fully extended. The baffle halves 501 and 503 separate from one another except where they were welded along the line 507 (FIG. 10B) in the first welding operation.

In an actual assembly operation, plural completed baffles 437 would be placed on a lower envelope half 436 and an upper envelope half 434 would be placed over the baffles. This assembly would be placed between plural concentric circular (in the case of circular baffles) welding electrodes, one per baffle, and all the baffles would be attached to the upper and lower envelope halves in a single welding operation. An additional concentric welding electrode could be provided to weld the outer peripheries 445 (FIG. 9B) of the upper and lower envelope halves together in the same operation.

When the inner-most baffle 467 is formed by the process just described, the lifting flange 448 is formed and the semi-annular portions 56 of the epsilon 54 are attached to it in a single welding operation. The area bounded by the phantom line 111 over which the baffle halves welded to one another is wider for the inner-most baffle 467 than for the remainder of the baffles 437, and has substantially the same width as the semi-annular portions 56.

Although the alternative embodiment of the body wall engaging element has been described with reference to the embodiment of the flexible lifting element described above with respect to FIGS. 1A–1F, the alternative embodiment of the body wall engaging element can also be used with the alternative embodiments of the flexible lifting element described above with respect to FIGS. 6A–6C, 7A–7C and 8A–8C.

The lifting apparatus according to the invention is used to lift a body wall according to the method to be described next with reference to FIGS. 11A–11H. A method of using the embodiment 10 of the lifting apparatus shown in FIGS. 1A–1F for lifting the lower abdominal wall will be described as an example. The method described can readily be adapted to lift other body walls using any of the alternative embodiments of the lifting apparatus described above.

Figure 11A:
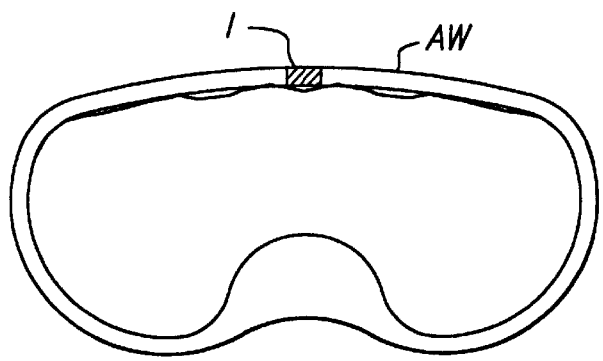
FIGS. 11A through 11L illustrate the method according to the invention of using the lifting apparatus according to the invention to lift the abdominal wall as an example of a body wall. These figures all show a transverse cross section of the abdomen. In these figures.
Figure 11B:
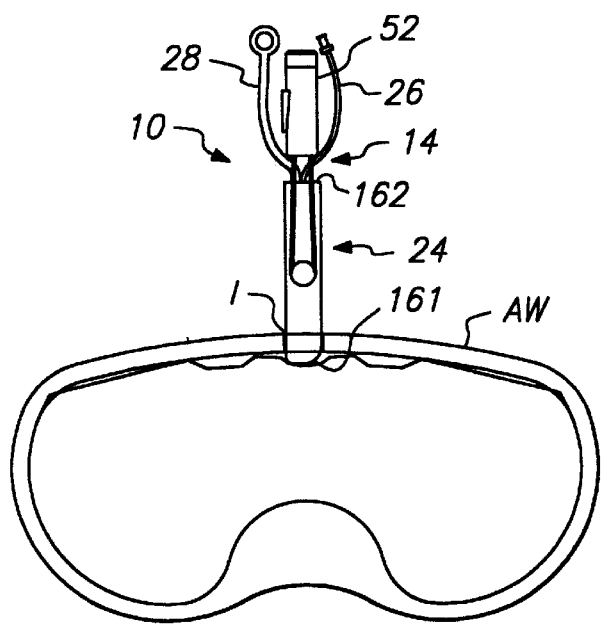

The lifting site is defined according to the treatment procedure that will follow the lifting. The center of the lifting site is then determined and a laparoscopic incision I is made through the abdominal wall AW, as shown in FIG. 11A. The laparoscopic incision is normally between 10 and 15 mm long, depending on the cross sectional dimensions of the packaged body wall engaging element 24. Alternatively, a laparoscopic puncture of an equivalent size may be used. The proximal end 162 of the packaged body wall engaging element 24 is grasped, and the distal end 161 of the package is then inserted into the incision, as shown in FIG. 11B. The inflation tube 26 and the tether 28 extend from the proximal end 162 of the package and lie adjacent to the arm attachment element 52. They may temporarily be attached to the arm attachment element for convenience during this part of the procedure.

Figure 11C:
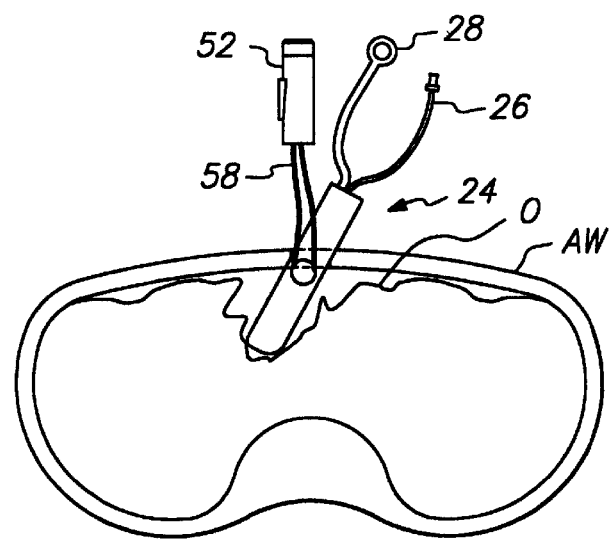
Figure 11D:
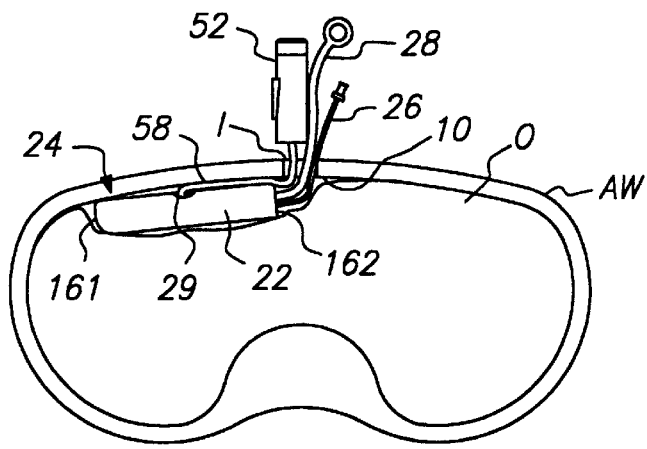

The packaged body wall engaging element 24 is then advanced through the incision I in the abdominal wall AW until the proximal end 162 of the package clears the peritoneum P, as shown in FIGS. 11C and 11D. As the packaged body wall engaging element is advanced through the abdominal wall, it is turned laterally, and the blunt, rounded distal tip 161 gently displaces the underlying viscera O downwards, away from the abdominal wall, and sideways, as shown in FIG. 11C.

FIG. 11D shows the packaged body wall engaging element following its insertion though the abdominal wall. The packaged body wall engaging element lies between the peritoneum P and the viscera O with the proximal end 162 of the package 24 adjacent the incision I. The strap 58 of the flexible lifting element extends from the aperture 29 in the pouch, and runs between the pouch and the peritoneum to exit through the abdominal wall at the incision I. The inflation tube 26 and the tether 28 also exit through the abdominal wall at the incision.

Figure 11E:
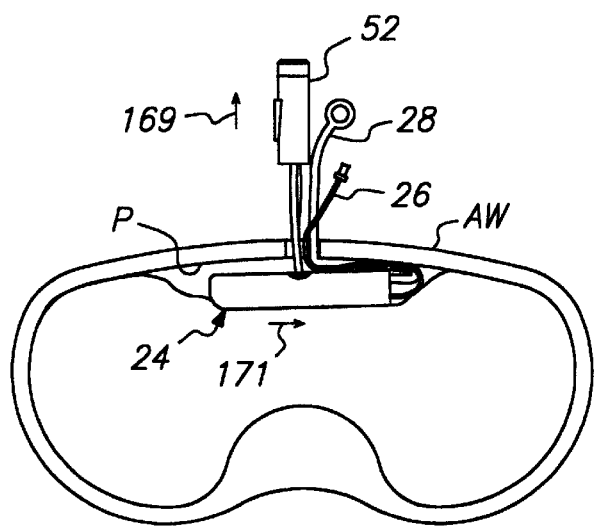
Figure 11F:
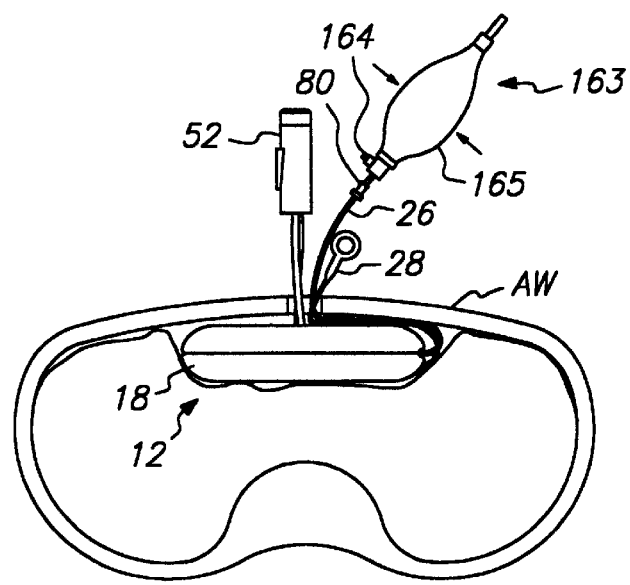

The arm attachment element 52 is then grasped and pulled proximally in the direction shown by the arrow 169 until a resistance is felt. Pulling the arm attachment element moves the packaged lifting apparatus 24 laterally, as indicated by the arrow 171 until the aperture 29 in the pouch 22 (and, hence, the central hole 32 of the body wall engaging element) is aligned with the incision I, as shown in FIG. 11E.

The bulb inflator 163 is then connected to the valve 80, and the bulb 165 is squeezed to feed inflation fluid, e.g., air, into the body wall engaging element 12. The inflation fluid causes the packaged body wall engaging element 12 to unroll slightly. The resulting tension on the pouch 22 ruptures the pouch along the perforations 103 (FIG. 2A). This releases the envelope 18 from the package. Release of the envelope from the package can be sensed by an abrupt drop in resistance to squeezing the bulb 165. After the envelope has been released from the pouch 22, the pouch remains attached to the body wall engaging element by the inflation tube 26 and the strap 58. The opened pouch is omitted from the Figures for clarity.

The bulb 165 is then squeezed an additional number of times to feed more inflation fluid into the body wall engaging element 12. This inflates the body wall engaging element. As the body wall engaging element inflates it first unrolls fully, spreading laterally, and then inflates, spreading axially. This motion of the body wall engaging element keeps the viscera O out of the contact area between the body wall engaging element 12 and the abdominal wall. The bulb 165 is squeezed until the sound of air being vented from the valve 80 indicates that the pressure in the body wall engaging element has reached the working pressure set by the valve 80. The working pressure is high enough to provide the required degree of stiffness in the body wall engaging element, but is not so high as to compromise the reliability of the lifting apparatus. The bulb inflator 163 may be disconnected from the valve 80 at the end of the inflation operation. A one-way element in the valve 80 maintains the inflation pressure in the body wall engaging element when the bulb inflator is disconnected.

Figure 11G:
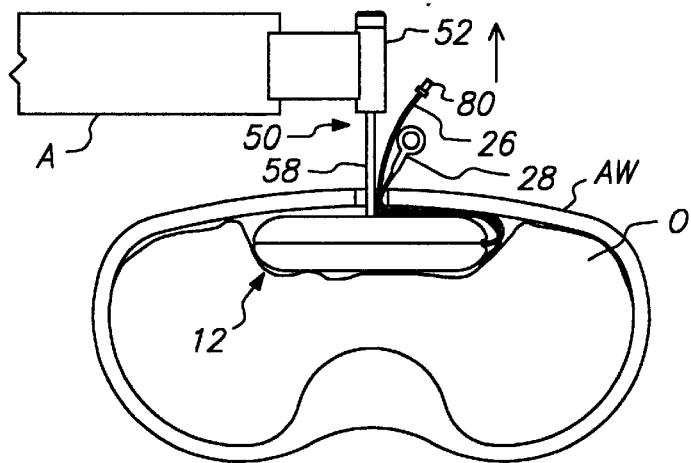

When the body wall engaging element 12 is in its fully inflated state, the arm attachment element 52 is attached to the lifting arm A using the dovetail connector, as shown in FIG. 11G. Raising the lifting arm A applies a lifting force to the arm attachment element, and thence, via the flexible element 50, to the body wall engaging element 12. The lifting surface 16 of the body wall engaging element applies the lifting force to a large area of the abdominal wall AW, which raises the abdominal wall to the position shown in FIG. 11H. Lifting the abdominal wall creates the working space WS between the underside of the body wall engaging element 12 and the underlying organs O. When the abdominal wall is in its lifted state, part of the inflation tube 26 and part of the tether 28 run between the lifting surface 16 and the peritoneum P. These parts are not shown in FIGS. 11H and 11I.

During the lifting operation, the body wall engaging element 12 may deform. If, as a result, the inflation pressure therein increases to a level approaching that which could compromise the reliability of the body wall engaging element, the valve 80 releases inflation fluid. This prevents the inflation pressure from increasing further, and maintains the reliability of the lifting apparatus.

Figure 11H:
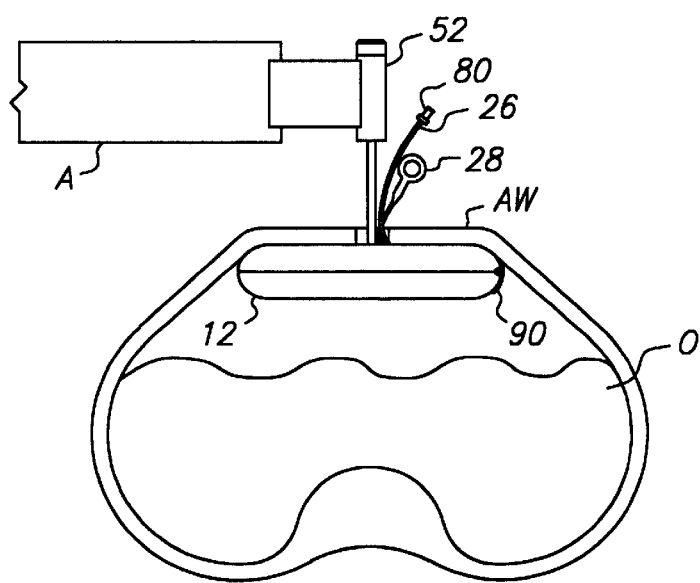
Figure 11I:
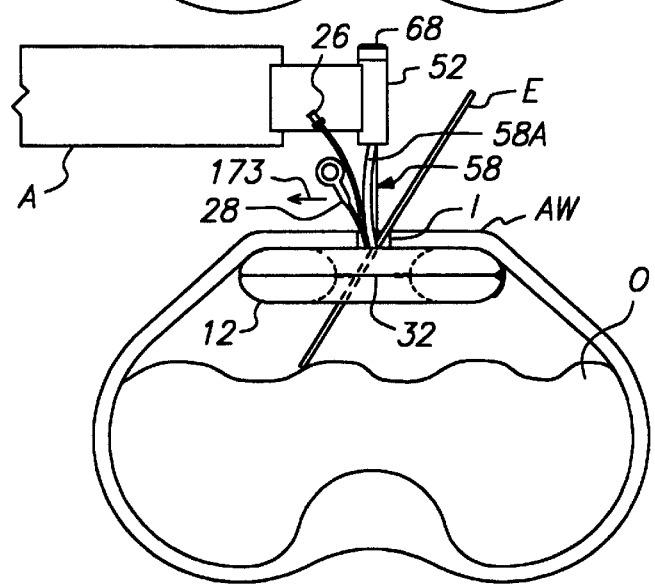

Before, during, or after the raising operation, an endoscope E, shown schematically in FIG. 11I, can be inserted into the incision I, and through the abdominal wall and the central hole 32 in the body wall engaging element to observe the underlying organs O. In FIG. 11I, the parts of the body wall engaging element 12 bounding the central hole 32 are shown to indicate the freedom of lateral movement provided by the large central hole 32 for the endoscope. FIG. 11I also shows the inflation tube 26, the tether 28 and one side 58A of the strap moved in the direction of the arrow 173 out of the way of the endoscope. The knob 68 of the arm attachment element 52 may be rotated to change the position of the strap 58.

The endoscope can be left in position during the treatment procedure that follows the lifting procedure, and one or more surgical instruments can be passed into the working space through the incision and the central hole 32. A trocar tube can be inserted into the incision and through the central hole 32 once the abdominal wall has been lifted to provide a clean passage into the underlying working space. Additional instruments can be inserted into the working space through the incision I, or through trocar tubes driven through the abdominal wall AW outside the outer periphery of the body wall engaging element.

At the end of the treatment procedure, the lifting arm A is lowered to restore the abdominal wall AW to its original (non-lifted) state. While the lifting arm is lowered, the flexibility of the strap 58 and ability of the dovetail connection between the dovetail connector (FIG. 5) on the arm attachment element and the lifting arm to disconnect together minimize the risk of the lifting arm applying a downwards force to the organs underlying the lifting apparatus.

Figure 11J:
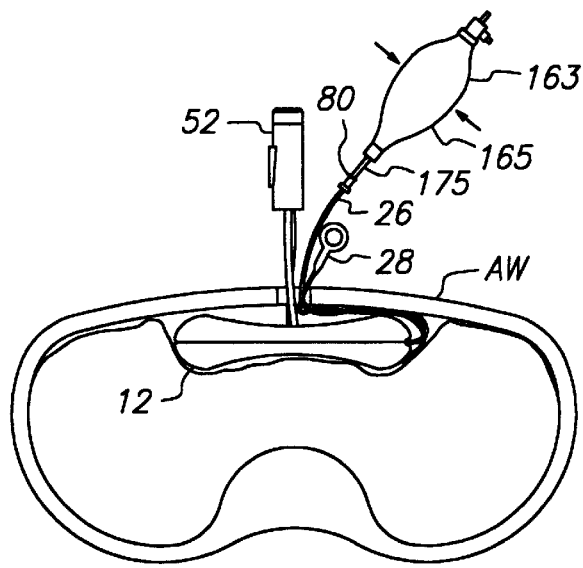

The arm attachment element 52 is disconnected from the lifting arm A, and the inlet connector 175 of bulb inflator 163 is connected to the valve 80, as shown in FIG. 11J. This releases the inflation fluid from the body wall engaging element 12. The bulb 165 is then squeezed a number of times to evacuate the inflation fluid from the body wall engaging element. After the body wall engaging element is fully evacuated, it assumes the flat, disc-like shape shown in FIG. 11K.

Figure 11K:
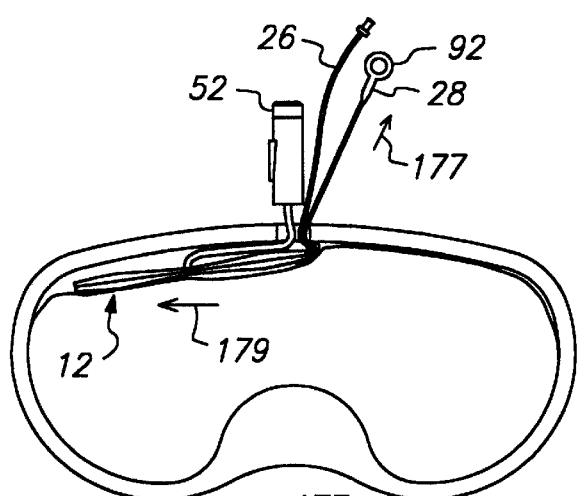
Figure 11L:
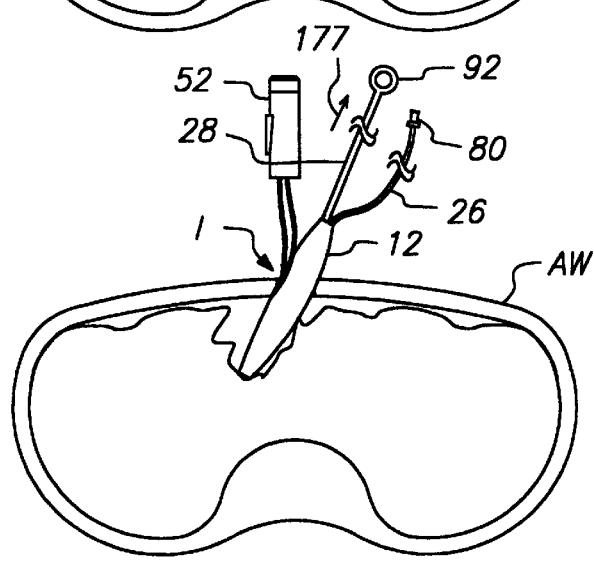

The proximal end 92 of the tether 28 is then gently pulled proximally, as indicated by the arrow 177. This moves the evacuated body wall engaging element 12 laterally in the direction shown by the arrow 179 to align the part of the outer periphery to which the distal end 90 of the tether 28 is attached with the incision I, as shown in FIG. 11K. Additional tension is then applied to the proximal end 92 of the tether pulls the portion of the evacuated body wall engaging element to which it is attached through the incision. This enables the evacuated body wall engaging element to be withdrawn edge-first from the abdominal cavity through the incision I, as shown in FIG. 11L. The arm attachment element 52 is also pulled proximally during this process. The incision is then closed to finish the procedure.

The lifting apparatus 10 may be used to lift a body wall manually, without the assistance of the lifting arm A. In this case, the body wall engaging element 12 is deployed under the body wall using the procedure described above with reference to FIGS. 11A–11F. Then, when the body wall engaging element is fully inflated, instead of connecting the arm engaging element 52 to the lifting arm, the surgeon grips the arm engaging element 52 and applies a lifting force to it. This raises the abdominal wall as shown in FIG. 11H. The endoscope E can then be inserted into the incision and through the central hole 32 to provide viewing of the working space WS, as shown in FIG. 11I.

In an embodiment of the lifting apparatus according to the invention intended for manual lifting applications, an element specially shaped to facilitate manual gripping can be substituted for the arm engaging element 52. Alternatively, the arm engaging element can be dispensed with entirely, and the lifting force can be applied manually directly to the strap 58.

It is envisaged that the manual lifting technique just described will be used especially in emergency rooms and trauma centers to lift relatively small areas of body walls to provide short-term observation of the underlying organs.

Although illustrative embodiments of the invention have been described herein in detail, it is to be understood that the invention is not limited to the precise embodiments described, and that various modifications may be practiced within the scope of the invention defined by the appended claims.

We claim:

1. A method of packaging a lifting apparatus for deployment through a laparoscopic incision, the method comprising steps of:
   providing a lifting apparatus comprising a flat body wall engaging element having a center, an outer periphery, and opposed faces, and having a flexible lifting element attached to approximately the center and extending from one of the faces, the flexible lifting element and body wall engaging element attached to permit relative pivotal movement between them;
   providing an elongate pouch having an open end and having on one side a central aperture and on the other side a longitudinal line of perforations;
   rolling the body wall engaging element from diametrically opposed points on the outer periphery towards the center, the body wall engaging element, after rolling, being substantially cylindrical;
   threading the flexible lifting element into the open end of the pouch and out of the central aperture of the pouch; and
   inserting the rolled body wall engaging element into the pouch.

2. The method of claim 1, wherein:
   in the step of rolling the body wall engaging element from diametrically-opposed points on the outer periphery towards the center, the diametrically-opposed points on the outer periphery of the body wall engaging element are rolled away from the flexible lifting element; and
   in the step of inserting the rolled body wall engaging element into the pouch, the rolled body wall engaging element is inserted into the pouch with the rolled portions thereof facing the line of perforations, and the flexible lifting element facing the central aperture.

3. Apparatus for deployment through a laparoscopic incision in a body wall to apply an external lifting force over a large area of the body wall, the apparatus comprising:
   a body wall engaging element capable of passing in a packaged state through the laparoscopic incision, and being inflatable to an inflated state in which the body wall engaging element is substantially toroidal, provides a broad lifting face, and bounds a central hole in the body wall engaging element extending through the broad lifting face, the body wall engaging element including an equatorial portion facing into the central hole; and
   a flexible lifting element, including:
      a flexible portion capable of passing through the laparoscopic incision, the flexible portion being attached to the equatorial portion of the body wall engaging element and positioned leaving the central hole at least partially exposed, and
      adapter means, connected to part of the flexible portion remote from the equatorial portion of the body wall engaging element, for receiving the external lifting force and for transferring the external lifting force to the flexible portion.

4. The apparatus of claim 3, wherein the body wall engaging element has a height and a radial width, the height being less than one half of the radial width.

5. The apparatus of claim 3, additionally comprising inflation tube means for inflating the body wall engaging element, the inflation tube means including pressure control means for limiting pressure in the body wall engaging element.

6. The apparatus of claim 3, additionally comprising inflation tube means for inflating the body wall engaging element, the inflation tube means including anti-kinking means for preventing kinking of the inflation tube means.

7. A method of applying an external lifting force of greater than ten pounds to a large area of a body wall to lift the body wall, the external lifting force being applied to the body wall through a laparcoscopic incision in the body wall, the method comprising steps of:
   providing a lifting apparatus, the lifting apparatus including:
      a body wall engaging element in a packaged state, capable of passing through the laparoscopic incision, the body wall engaging element being inflatable from the packaged state to an inflated state wherein the body wall engaging element is substantially toroidal, provides a broad lifting face, and bounds a central hole in the body wall engaging element extending through the broad lifting face, the body wall engaging element in the packaged state being a packaged body wall engaging element, and
      a flexible lifting element, including:
         a flexible portion capable of passing through the laparoscopic incision, the flexible portion being attached to the equatorial portion of the body wall engaging element and positioned leaving the central hole at least partially exposed, and
         adapter means, connected to part of the flexible portion remote from the equatorial portion of the body wall engaging element, for receiving the external lifting force and for transferring the external lifting force to the flexible portion;
   advancing the packaged body wall engaging element and part of the flexible lifting element through the laparoscopic incision;
   inflating the body wall engaging element to an inflated state to provide a broad lifting surface; and
   applying the external lifting force to the adapter means of the flexible lifting element to move the broad lifting surface into contact with the body wall and to lift the body wall from a normal state to a lifted state.

8. The method of claim 7, wherein:
   in the step of providing a lifting apparatus, the packaged body wall engaging element is housed in a pouch, the pouch including a central aperture wherefrom the flexible lifting element emerges, and a portion divided by a line of perforations; and
   in the step of inflating the body wall engaging element, initial inflation of the body wall engaging element bursts the pouch at the line of perforations and releases the body wall engaging element from the pouch.

9. The method of claim 7, wherein, following the step of applying the lifting force to the adapter means, the method additionally comprises a step of moving the body wall laterally relative to the adapter means.

10. The method of claim 7, wherein:
    in the step of providing a lifting apparatus, a lifting apparatus having an inflation tube connected to the body wall engaging element is provided, the inflation tube being fitted with pressure relief valve means for venting inflation fluid to limit pressure in the body wall engaging element; and
    in the step of inflating the body wall engaging element, the body wall engaging element is inflated until the pressure relief valve means vents.

11. An apparatus for deployment through a laparoscopic incision in a body wall to apply an external lifting force over a large area of the body wall, the apparatus comprising:

a body wall engaging element capable of passing in a packaged state through the laparoscopic incision, and being inflatable to an inflated state in which the body wall engaging element provides a broad lifting face having a hole extending therethrough; and a flexible lifting element, including:
- a flexible portion capable of passing through the laparoscopic incision, the flexible portion being attached to the body wall engaging element adjacent to the hole and positioned leaving the hole at least partially exposed, and
- a lifting adapter connected to part of the flexible portion remote from the body wall engaging element.

12. A method of packaging a lifting apparatus for deployment through a laparoscopic incision, the method comprising steps of:

providing a lifting apparatus comprising a flat body wall engaging element having an outer periphery, opposed faces, a hole extending through the broad faces, and a flexible lifting element attached to the body wall engaging elements adjacent to the hole and positioned leaving the hole at least partially exposed;

providing an elongate pouch having an open end and having on one side a central aperture and on the other side a longitudinal line of perforations;

rolling the body wall engaging element from diametrically opposed points on the outer periphery towards the center, the body wall engaging element, after rolling, being substantially cylindrical;

threading the flexible lifting element into the open end of the pouch and out of the central aperture of the pouch; and inserting the rolled body wall engaging element into the pouch.

* * * * *